(12) United States Patent
Fell et al.

(10) Patent No.: US 7,531,534 B2
(45) Date of Patent: *May 12, 2009

(54) HETEROCYCLIC ANTIVIRAL COMPOUNDS

(75) Inventors: Jay Bradford Fell, Longmont, CO (US); Peter Mohr, Longmont, CO (US); Peter J. Stengel, Longmont, CO (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/706,777

(22) Filed: Feb. 15, 2007

(65) Prior Publication Data

US 2008/0095739 A1 Apr. 24, 2008

Related U.S. Application Data

(60) Provisional application No. 60/774,419, filed on Feb. 17, 2006.

(51) Int. Cl.
C07D 417/02 (2006.01)
A61K 31/5415 (2006.01)

(52) U.S. Cl. ..................... 514/224.2; 544/52
(58) Field of Classification Search ............ 544/52; 514/224.2
See application file for complete search history.

(56) References Cited

U.S. PATENT DOCUMENTS

| 2004/0087577 A1 | 5/2004 | Pratt et al. |
|---|---|---|
| 2004/0097492 A1 | 5/2004 | Pratt et al. |
| 2004/0162285 A1 | 8/2004 | Pratt et al. |
| 2004/0167123 A1 | 8/2004 | Pratt et al. |
| 2005/0075331 A1 | 4/2005 | Pratt et al. |

FOREIGN PATENT DOCUMENTS

| WO | WO 01/85172 A1 | 11/2001 |
|---|---|---|
| WO | WO02/098424 A1 | 12/2002 |
| WO | WO 03/037262 A2 | 5/2003 |
| WO | WO 03/099801 A1 | 12/2003 |
| WO | WO 2004/041818 A1 | 5/2004 |
| WO | WO 2004/052313 A2 | 6/2004 |
| WO | WO 2004/058150 A2 | 7/2004 |
| WO | WO 2006/021340 A1 | 3/2006 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*

* cited by examiner

*Primary Examiner*—Kahsay T Habte
(74) *Attorney, Agent, or Firm*—Brian L. Buckwalter

(57) ABSTRACT

Compounds having the formula Ia or Ib wherein $R^1$, $R^2$, $R^3$ and $R^4$ are as defined herein are Hepatitis C virus NS5b polymerase inhibitors. Also disclosed are compositions and methods for treating an HCV infection and inhibiting HCV replication.

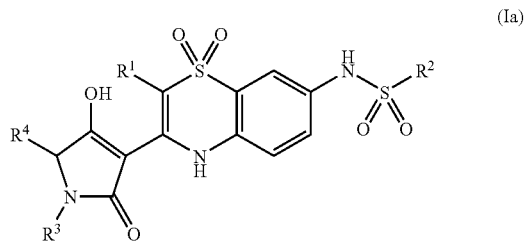

(Ia)

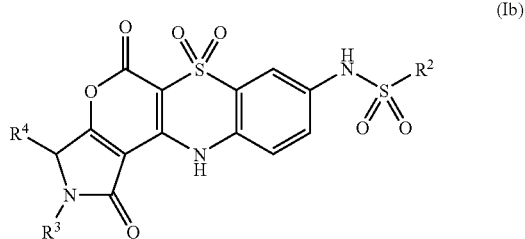

(Ib)

15 Claims, No Drawings

HETEROCYCLIC ANTIVIRAL COMPOUNDS

CROSS REFERENCE TO PRIOR APPLICATIONS

This application claims the benefit of priority to U.S. Ser. No. 60/774,419 filed Feb. 17, 2006 the contents of which are hereby incorporated in their entirety by reference.

FIELD OF THE INVENTION

The present invention provides non-nucleoside compounds and certain derivatives thereof which are inhibitors of RNA-dependent RNA viral polymerase. These compounds are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND

Hepatitis C virus is the leading cause of chronic liver disease throughout the world. (Boyer, N. et al., *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., *Flaviviridae: The viruses and their replication.* In: *Fields Virology*, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forms and J. Bukh, *Clinics in Liver Disease* 1999 3:693-716; J. Bukh et al., *Semin. Liv. Dis.* 1995 15:41-63). Unfortunately Type 1 infectious is more resistant to therapy than either type 2 or 3 genotypes (N. N. Zein, *Clin. Microbiol. Rev.*, 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of non-structural protein 5) remain unknown. It is believed that most of the non-structural proteins encoded by the HCV RNA genome are involved in RNA replication Currently a limited number of approved therapies are available for the treatment of HCV infection. New and existing therapeutic approaches to treating HCV and inhibition of HCV NS5B polymerase have been reviewed: R. G. Gish, *Sem. Liver. Dis.*, 1999 19:5; Di Besceglie, A. M. and Bacon, B. R., Scientific American, October: 1999 80-85; G. Lake-Bakaar, *Current and Future Therapy for Chronic Hepatitis C Virus Liver Disease, Curr. Drug Targ. Infect Dis.* 2003 3(3): 247-253; P. Hoffmann et al., *Recent patents on experimental therapy for hepatitis C virus infection* (1999-2002), *Exp. Opin. Ther. Patents* 2003 13(11):1707-1723; M. P. Walker et al., *Promising Candidates for the treatment of chronic hepatitis C, Exp. Opin. Investing. Drugs* 2003 12(8):1269-1280; S.-L. Tan et al., *Hepatitis C Therapeutics: Current Status and Emerging Strategies, Nature Rev. Drug Discov.* 2002 1:867-881; J. Z. Wu and Z. Hong, *Targeting NS5B RNA-Dependent RNA Polymerase for Anti-HCV Chemotherapy, Curr. Drug Targ.-Infect. Dis.* 2003 3(3):207-219.

Ribavirin (1-((2R,3R,4S,5R)-3,4-Dihydroxy-5-hydroxymethyl-tetrahydro-furan-2-yl)-1H-[1,2,4]triazole-3-carboxylic acid amide; Virazole®) is a synthetic, non-interferon-inducing, broad spectrum antiviral nucleoside analog. Ribavirin has in vitro activity against several DNA and RNA viruses including Flaviviridae (Gary L. Davis. *Gastroenterology* 2000 118:S104-S114). Although, in monotherapy ribavirin reduces serum amino transferase levels to normal in 40% or patients, it does not lower serum levels of HCV-RNA. Ribavirin also exhibits significant toxicity and is known to induce anemia. Viramidine is a ribavirin prodrug converted to in hepatocytes.

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon β, type 2 includes interferon γ. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

One limitation of early IFN therapy was rapid clearance of the protein from the blood. Chemical derivatization of IFN with polyethyleneglycol (PEG) has resulted in proteins with substantially improved pharmacokinetic properties. PEGA-SYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release*, 2001 72:217-224).

Combination therapy of HCV with ribavirin and interferon-α currently is the optimal therapy for HCV. Combining ribavirin and PEG-IFN (infra) results in a sustained viral response (SVR) in 54-56% of patients with type 1 HCV. The SVR approaches 80% for type 2 and 3 HCV. (Walker, supra) Unfortunately, combination therapy also produces side effects which pose clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2-NS3 autoprotease, the NS3 protease, the NS3 helicase and the NS5B polymerase. The RNA-dependent RNA polymerase is absolutely essential for replication of the single-stranded, positive sense, RNA genome. This enzyme has elicited significant interest among medicinal chemists.

Nucleoside inhibitors can act either as a chain terminator or as a competitive inhibitor that interferes with nucleotide binding to the polymerase. To function as a chain terminator the nucleoside analog must be taken up be the cell and converted in vivo to a triphosphate to compete for the polymerase nucleotide binding site. This conversion to the triphosphate is commonly mediated by cellular kinases which imparts additional structural limitations on any nucleoside. In addition this limits the direct evaluation of nucleosides as inhibitors of HCV replication to cell-based assays (J. A. Martin et al., U.S. Pat. No. 6,846,810; C. Pierra et al., *J. Med. Chem.* 2006 49(22): 6614-6620; J. W. Tomassini et al., *Antimicrob. Agents and Chemother.* 2005 49(5):2050; J. L. Clark et al., *J. Med. Chem.* 2005 48(17):2005).

Non-nucleoside allosteric inhibitors of HIV reverse transcriptase have proven effective therapeutics alone and in combination with nucleoside inhibitors and with protease inhibitors. Several classes of non-nucleoside HCV NS5B inhibitors have been described and are currently at various stages of development including: benzimidazoles, (H. Hashimoto et al. WO 01/47833, H. Hashimoto et al. WO 03/000254, P. L. Beaulieu et al. WO 03/020240 A2; P. L. Beaulieu et al. U.S. Pat. No. 6,448,281 B1; P. L. Beaulieu et al. WO 03/007945 A1); indoles, (P. L. Beaulieu et al. WO 03/0010141 A2); benzothiadiazines, e.g., 1, (D. Dhanak et al. WO 01/85172 A1, filed May 10, 2001; D. Chai et al., WO2002098424, filed Jun. 7, 2002, D. Dhanak et al. WO 03/037262 A2, filed Oct. 28, 2002; K. J. Duffy et al. WO03/099801 A1, filed May 23, 2003, M. G. Darcy et al. WO2003059356, filed Oct. 28, 2002; D. Chai et al. WO 2004052312, filed Jun. 24, 2004, D. Chai et al. WO2004052313, filed Dec. 13, 2003; D. M. Fitch et al., WO2004058150, filed Dec. 11, 2003; D. K. Hutchinson et al. WO2005019191, filed Aug. 19, 2004; J. K. Pratt et al. WO 2004/041818 A1, filed

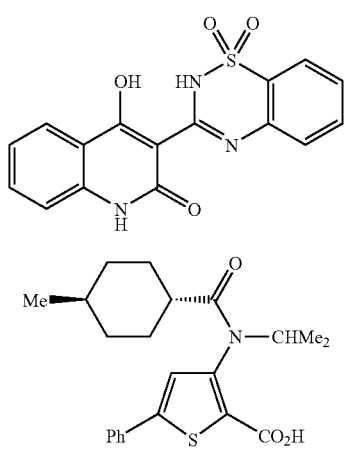

Oct. 31, 2003); thiophenes, e.g., 2, (C. K. Chan et al. WO 02/100851 A2); benzothiophenes (D. C. Young and T. R. Bailey WO 00/18231); β-ketopyruvates (S. Attamura et al. U.S. Pat. No. 6,492,423 B1, A. Attamura et al. WO 00/06529); pyrimidines (C. Gardelli et al. WO 02/06246 A1); pyrimidinediones (T. R. Bailey and D. C. Young WO 00/13708); triazines (K.-H. Chung et al. WO 02/079187 A1); rhodanine derivatives (T. R. Bailey and D. C. Young WO 00/10573, J. C. Jean et al. WO 01/77091 A2); 2,4-dioxopyrans (R. A. Love et al. EP 256628 A2); phenylalanine derivatives (M. Wang et al. *J. Biol. Chem.* 2003 278:2489-2495).

1,1-Dioxo-4H-benzo[1,4]thiazin-3-yl derivatives that inhibit HCV NS5B have been disclosed by J. F. Blake et al. in U.S. Publication No. 20060252785. 1,1-Dioxo-benzo[d]isothazol-3-yl that inhibits HCV NS5B have been disclosed by J. F. Blake et al. in U.S. Publication No. 2006040927.

SUMMARY OF THE INVENTION

The present invention is directed toward novel heterocyclic compounds that inhibit HCV polymerase, methods of treating a disorder mediated by HCV with said compounds and pharmaceutical compositions containing said compound which compound possesses a structure according to formula Ia or Ib

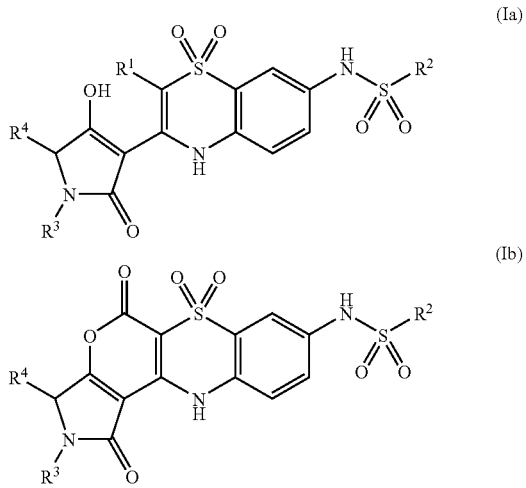

wherein:

$R^1$ is halogen, $C_{1-3}$ alkyl, $COR^5$, $CH_2COR^5$, CN or $CH_2CN$;

$R^2$ is $C_{1-6}$ alkyl, $C_{3-7}$ cycloalkyl, $C_{3-7}$ cycloalkyl-$C_{1-3}$ alkyl, phenyl-$C_{1-3}$ alkyl, $NR^aR^b$ or phenyl wherein said phenyl rings are optionally substituted with 1 to 3 groups independently selected in each occurrence from the group consisting of $C_{1-6}$ alkyl, $C_{1-6}$ alkoxy, halogen, $NR^aR^b$ and cyano;

$R^3$ is $C_{1-6}$ alkyl, $C_{3-7}$ cycloalkyl-$C_{1-3}$ alkyl or phenyl-$C_{1-3}$ alkyl wherein said phenyl is optionally substituted with 1 to 3 groups independently selected in each occurrence from the group consisting of $C_{1-6}$ alkyl, $C_{1-6}$ alkoxy, halogen, $NR^aR^b$, nitro and cyano, or pyridinyl-methyl said pyridinyl optionally substituted with halogen;

$R^4$ is $C_{1-6}$ alkyl or $C_{3-7}$ cycloalkyl;

$R^5$ is OH, $C_{1-6}$ alkoxy, $NR^cR^d$;

$R^a$ and $R^b$ (i) taken independently in each occurrence are hydrogen or $C_{1-6}$ alkyl or (ii) taken together are $(CH_2)_n$ wherein n is 4-6 or $(CH_2)_2X(CH_2)_2$ wherein X is O, S, $NR^c$;

$R^c$ and $R^d$ are independently hydrogen or $C_{1-6}$ alkyl; or, pharmaceutically acceptable salts, hydrates and solvates thereof.

Compounds of the present invention are further useful for inhibiting HCV polymerase in cells infected by HCV.

DETAILED DESCRIPTION OF THE INVENTION

In one embodiment of the present invention there is provided a compound according to formula Ia or Ib wherein $R^1$, $R^2$, $R^3$, $R^4$, $R^5$, $R^a$, $R^b$, $R^c$, $R^d$, X and n are as defined herein above. The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

In another embodiment of the present invention there is provided a compound according to formula Ia wherein $R^1$, $R^2$, $R^3$, $R^4$, $R^5$, $R^a$, $R^b$, $R^c$, $R^d$, X and n are as defined herein above.

$R^3$ is $C_{1-6}$ alkyl, $C_{3-7}$ cycloalkyl-$C_{1-3}$ alkyl or phenyl-$C_{1-3}$ alkyl wherein said phenyl is optionally substituted with 1 to 3 groups independently selected in each occurrence from the group consisting of $C_{1-6}$ alkyl, $C_{1-6}$ alkoxy, halogen, $NR^aR^b$, nitro and cyano, or pyridinyl-methyl said pyridinyl optionally substituted with halogen; and, $R^1$, $R^2$, $R^4$, $R^5$, $R^a$, $R^b$, $R^c$, $R^d$, X and n are as defined herein above.

In another embodiment of the present invention there is provided a compound according to formula Ia wherein $R^1$ is halogen; $R^2$ is $C_{1-6}$ alkyl or $C_{3-7}$ cycloalkyl; $R^3$ is $C_{1-6}$ alkyl, $C_{3-7}$ cycloalkyl-$C_{1-3}$ alkyl or phenyl-$C_{1-3}$ alkyl wherein said phenyl is optionally substituted with 1 to 3 groups independently selected in each occurrence from the group consisting of $C_{1-6}$ alkyl, $C_{1-6}$ alkoxy, halogen, $NR^aR^b$, nitro and cyano; $R^4$ is $C_{1-6}$ alkyl; and, $R^5$, $R^a$, $R^b$, $R^c$, $R^d$, X and n are as defined herein above.

In another embodiment of the present invention there is provided a compound according to formula Ia wherein $R^1$ is halogen; $R^2$ is $C_{1-6}$ alkyl or $C_{3-7}$ cycloalkyl; $R^3$ is $C_{1-6}$ alkyl or phenyl-$C_{1-3}$ alkyl wherein said phenyl is optionally substituted with 1 to 3 groups independently selected in each occurrence from the group consisting of $C_{1-6}$ alkyl, halogen and $C_{1-6}$ alkoxy; $R^4$ is $C_{1-6}$ alkyl; and, $R^5$, $R^a$, $R^b$, $R^c$, $R^d$, X and n are as defined herein above.

In another embodiment of the present invention there is provided a compound according to formula Ia wherein $R^1$ is halogen; $R^2$ is $C_{1-6}$ alkyl; $R^3$ is $C_{1-6}$ alkyl or phenyl-$C_{1-3}$ alkyl wherein said phenyl is optionally substituted with 1 to 3 groups independently selected in each occurrence from the group consisting of $C_{1-6}$ alkyl, halogen and $C_{1-6}$ alkoxy; $R^4$ is $C_{1-6}$ alkyl; and, $R^5$, $R^a$, $R^b$, $R^c$, $R^d$, X and n are as defined herein above.

In one embodiment of the present invention there is provided a compound according to formula Ia wherein $R^1$ is chloro; and, $R^2$, $R^3$, $R^4$, $R^5$, $R^a$, $R^b$, $R^c$, $R^d$, X and n are as defined herein above.

In one embodiment of the present invention there is provided a compound according to formula Ia wherein $R^1$ is halogen; $R^2$ is $NR^aR^b$; $R^3$ is $C_{1-6}$ alkyl; $C_{3-7}$ cycloalkyl-$C_{1-3}$ alkyl or phenyl-$C_{1-3}$ alkyl wherein said phenyl is optionally substituted with 1 to 3 groups independently selected in each occurrence from the group consisting of $C_{1-6}$ alkyl, $C_{1-6}$ alkoxy, halogen, $NR^aR^b$, nitro and cyano; $R^a$ and $R^b$ (i) taken independently in each occurrence are hydrogen or $C_{1-6}$ alkyl or (ii) taken together are $(CH_2)_n$ wherein n is 4-6; and, $R^4$, $R^5$, $R^c$, $R^d$ and X are as defined herein above.

In one embodiment of the present invention there is provided a compound according to formula Ia wherein $R^1$ is chloro; $R^2$ is $NR^aR^b$; $R^3$ is $C_{1-6}$ alkyl or phenyl-$C_{1-3}$ alkyl wherein said phenyl is optionally substituted with 1 to 3 groups independently selected in each occurrence from the group consisting of $C_{1-6}$ alkyl, $C_{1-6}$ alkoxy, halogen, $NR^aR^b$, nitro and cyano; $R^4$ is $C_{1-6}$ alkyl; $R^a$ and $R^b$ (i) taken independently in each occurrence are hydrogen or $C_{1-6}$ alkyl or (ii) taken together are $(CH_2)_n$ wherein n is 4-6; and, $R^4$, $R^5$, $R^c$, $R^d$, and X are as defined herein above.

In one embodiment of the present invention there is provided a compound according to formula Ia wherein $R^1$ is $C_{1-6}$ alkyl; and, $R^2$, $R^3$, $R^4$, $R^5$, $R^a$, $R^b$, $R^c$, $R^d$, X and n are as defined herein above.

In one embodiment of the present invention there is provided a compound according to formula Ia wherein $R^1$ and $R^2$ are $C_{1-6}$ alkyl; $R^3$ is $C_{1-6}$ alkyl or phenyl-$C_{1-3}$ alkyl wherein said phenyl is optionally substituted with 1 to 3 groups independently selected in each occurrence from the group consisting of $C_{1-6}$ alkyl, halogen or $C_{1-6}$ alkoxy; and, $R^4$, $R^5$, $R^a$, $R^b$, $R^c$, $R^d$, X and n are as defined herein above.

In one embodiment of the present invention there is provided a compound according to formula Ia wherein $R^1$ is $COR^5$; $R^5$ is $NR^cR^d$; and, $R^2$, $R^3$, $R^4$, $R^a$, $R^b$, $R^c$, $R^d$, X and n are as defined herein above.

In one embodiment of the present invention there is provided a compound according to formula Ia wherein $R^1$ is $COR^5$; $R^2$ is $C_{1-6}$ alkyl, $C_{3-7}$ cycloalkyl or $NR^aR^b$; $R^3$ is $C_{1-6}$ alkyl or phenyl-$C_{1-3}$ alkyl wherein said phenyl is optionally substituted with 1 to 3 groups independently selected in each occurrence from the group consisting of $C_{1-6}$ alkyl, $C_{1-6}$ alkoxy, halogen, $NR^aR^b$, nitro and cyano; $R^4$ is $C_{1-6}$ alkyl; $R^5$ is $NR^cR^d$; $R^c$ and $R^d$ are hydrogen; and, $R^a$, $R^b$, X and n are as defined herein above.

In one embodiment of the present invention there is provided a compound according to formula Ia wherein $R^1$ is $COR^5$; $R^2$ is methyl; $R^3$ is 4-F-benzyl; $R^4$ is tert-butyl; $R^5$ is $NR^cR^d$; $R^c$ and $R^d$ are hydrogen; and, $R^a$, $R^b$, X and n are as defined herein above.

In another embodiment of the present invention there is provided a compound according to formula Ib wherein $R^2$, $R^3$, $R^4$, $R^a$, $R^b$, $R^c$, $R^d$, X and n are as defined herein above.

In another embodiment of the present invention there is provided a compound for treatment of HCV which compound is:

N-{3-[(S)-5-tert-Butyl-1-(4-fluoro-benzyl)-4-hydroxy-2-oxo-2,5-dihydro-1H-pyrrol-3-yl]-2-methyl-1,1-dioxo-1,4-dihydro-1λ⁶-benzo[1,4]thiazin-7-yl}-methanesulfonamide, N-{3-[(S)-5-tert-Butyl-4-hydroxy-1-(3-methyl-butyl)-2-oxo-2,5-dihydro-1H-pyrrol-3-yl]-2-chloro-1,1-dioxo-1,4-dihydro-1λ⁶-benzo[1,4]thiazin-7-yl}-methanesulfonamide, N-{3-[(S)-5-tert-Butyl-1-(4-fluoro-benzyl)-4-hydroxy-2-oxo-2,5-dihydro-1H-pyrrol-3-yl]-2-chloro-1,1-dioxo-1,4-dihydro-1λ⁶-benzo[1,4]thiazin-7-yl}-methanesulfonamide, Ethanesulfonic acid {3-[(S)-5-tert-butyl-1-(4-fluoro-benzyl)-4-hydroxy-2-oxo-2,5-dihydro-1H-pyrrol-3-yl]-2-chloro-1,1-dioxo-1,4-dihydro-1λ⁶-benzo[1,4]thiazin-7-yl}-amide, Cyclopropanesulfonic acid {3-[(S)-5-tert-butyl-1-(4-fluoro-benzyl)-4-hydroxy-2-oxo-2,5-dihydro-1H-pyrrol-3-yl]-2-chloro-1,1-dioxo-1,4-dihydro-1λ⁶-benzo[1,4]thiazin-7-yl}-amide, N-{3-[(S)-5-tert-Butyl-1-(4-fluoro-3-methyl-benzyl)-4-hydroxy-2-oxo-2,5-dihydro-1H-pyrrol-3-yl]-2-chloro-1,1-dioxo-1,4-dihydro-1λ⁶-benzo[1,4]thiazin-7-yl}-methanesulfonamide, Ethanesulfonic acid {3-[(S)-5-tert-butyl-1-(4-fluoro-3-methyl-benzyl)-4-hydroxy-2-oxo-2,5-dihydro-1H-pyrrol-3-yl]-2-chloro-1,1-dioxo-1,4-dihydro-1$\lambda^6$-benzo[1,4]thiazin-7-yl}-amide, Cyclopropanesulfonic acid {3-[(S)-5-tert-butyl-1-(4-fluoro-3-methyl-benzyl)-4-hydroxy-2-oxo-2,5-dihydro-1H-pyrrol-3-yl]-2-chloro-1,1-dioxo-1,4-dihydro-1$\lambda^6$-benzo[1,4]thiazin-7-yl}-amide, N-{3-[(S)-5-tert-Butyl-1-(3-chloro-4-fluoro-benzyl)-4-hydroxy-2-oxo-2,5-dihydro-1H-pyrrol-3-yl]-2-chloro-1,1-dioxo-1,4-dihydro-1$\lambda^6$-benzo[1,4]thiazin-7-yl}-methanesulfonamide, Ethanesulfonic acid {3-[(S)-5-tert-butyl-1-(3-chloro-4-fluoro-benzyl)-4-hydroxy-2-oxo-2,5-dihydro-1H-pyrrol-3-yl]-2-chloro-1,1-dioxo-1,4-dihydro-1$\lambda^6$-benzo[1,4]thiazin-7-yl}-amide, Cyclopropanesulfonic acid {3-[(S)-5-tert-butyl-1-(3-chloro-4-fluoro-benzyl)-4-hydroxy-2-oxo-2,5-dihydro-1H-pyrrol-3-yl]-2-chloro-1,1-dioxo-1,4-dihydro-1$\lambda^6$-benzo[1,4]thiazin-7-yl}-amide, Ethanesulfonic acid {3-[(S)-5-tert-butyl-4-hydroxy-1-(3-methyl-butyl)-2-oxo-2,5-dihydro-1H-pyrrol-3-yl]-2-chloro-1,1-dioxo-1,4-dihydro-1$\lambda^6$-benzo[1,4]thiazin-7-yl}-amide, N-{3-[(S)-5-tert-Butyl-1-(5-fluoro-pyridin-2-ylmethyl)-4-hydroxy-2-oxo-2,5-dihydro-1H-pyrrol-3-yl]-2-chloro-1,1-dioxo-1,4-dihydro-1$\lambda^6$-benzo[1,4]thiazin-7-yl}-methanesulfonamide, N-[3-((S)-1-Benzyl-5-tert-butyl-4-hydroxy-2-oxo-2,5-dihydro-1H-pyrrol-3-yl)-2-chloro-1,1-dioxo-1,4-dihydro-1$\lambda^6$-benzo[1,4]thiazin-7-yl]-methanesulfonamide, N-{3-[(S)-5-tert-Butyl-1-(2-cyclopentyl-ethyl)-4-hydroxy-2-oxo-2,5-dihydro-1H-pyrrol-3-yl]-2-chloro-1,1-dioxo-1,4-dihydro-1$\lambda^6$-benzo[1,4]thiazin-7-yl}-methanesulfonamide, N-{3-[(S)-5-tert-Butyl-1-(4-fluoro-3-methoxy-benzyl)-4-hydroxy-2-oxo-2,5-dihydro-1H-pyrrol-3-yl]-2-chloro-1,1-dioxo-1,4-dihydro-1$\lambda^6$-benzo[1,4]thiazin-7-yl}-methanesulfonamide, N-{3-[(S)-5-tert-Butyl-1-(2-cyclopropyl-ethyl)-4-hydroxy-2-oxo-2,5-dihydro-1H-pyrrol-3-yl]-2-chloro-1,1-dioxo-1,4-dihydro-1$\lambda^6$-benzo[1,4]thiazin-7-yl}-methanesulfonamide, N-{3-[(S)-5-tert-Butyl-1-(4-fluoro-3-methyl-benzyl)-4-hydroxy-2-oxo-2,5-dihydro-1H-pyrrol-3-yl]-2-fluoro-1,1-dioxo-1,4-dihydro-1$\lambda^6$-benzo[1,4]thiazin-7-yl}-methanesulfonamide, N-{3-[(S)-5-tert-Butyl-1-(4-fluoro-benzyl)-4-hydroxy-2-oxo-2,5-dihydro-1H-pyrrol-3-yl]-2-cyano-1,1-dioxo-1,4-dihydro-1$\lambda^6$-benzo[1,4]thiazin-7-yl}-methanesulfonamide, 3-[(S)-5-tert-Butyl-1-(4-fluoro-benzyl)-4-hydroxy-2-oxo-2,5-dihydro-1H-pyrrol-3-yl]-7-methanesulfonylamino-1,1-dioxo-1,4-dihydro-1$\lambda^6$-benzo[1,4]thiazine-2-carboxylic acid amide, 3-[(S)-5-tert-Butyl-1-(4-fluoro-benzyl)-4-hydroxy-2-oxo-2,5-dihydro-1H-pyrrol-3-yl]-7-methanesulfonylamino-1,1-dioxo-1,4-dihydro-1$\lambda^6$-benzo[1,4]thiazine-2-carboxylic acid dimethylamide Cyclopropanesulfonic acid {3-[(S)-5-tert-butyl-4-hydroxy-1-(3-methyl-butyl)-2-oxo-2,5-dihydro-1H-pyrrol-3-yl]-2-chloro-1,1-dioxo-1,4-dihydro-1)-1$\lambda^6$-benzo[1,4]thiazin-7-yl}-amide, N-{3-[(S)-5-tert-Butyl-1-(3-chloro-4-fluoro-benzyl)-4-hydroxy-2-oxo-2,5-dihydro-1H-pyrrol-3-yl]-2-cyano-1,1-dioxo-1,4-dihydro-1$\lambda^6$-benzo[1,4]thiazin--7-yl}-methanesulfonamide, N-{3-[(S)-5-tert-Butyl-1-(4-fluoro-3-methoxy-benzyl)-4-hydroxy-2-oxo-2,5-dihydro-1H-pyrrol-3-yl]-2-cyano-1,1-dioxo-1,4-dihydro-1$\lambda^6$-benzo[1,4]thiazin-7-yl}-methanesulfonamide, N-{3-[(S)-5-tert-Butyl-1-(4-fluoro-3-methyl-benzyl)-4-hydroxy-2-oxo-2,5-dihydro-1H-pyrrol-3-yl]-2-cyano-1,1-dioxo-1,4-dihydro-1$\lambda^6$-benzo[1,4]thiazin-7-yl}-methanesulfonamide, N-{3-[(S)-5-tert-Butyl-4-hydroxy-1-(3-methyl-butyl)-2-oxo-2,5-dihydro-1H-pyrrol-3-yl]-2-cyano-1,1-dioxo-1,4-dihydro-1$\lambda^6$-benzo[1,4]thiazin-7-yl}-methanesulfonamide, N-{3-[(S)-5-tert-Butyl-1-(2-cyclopropyl-ethyl)-4-hydroxy-2-oxo-2,5-dihydro-1H-pyrrol-3-yl]-2-cyano-1,1-dioxo-1,4-dihydro-1$\lambda^6$-benzo[1,4]thiazin-7-yl}-methanesulfonamide, N-{3-[(S)-5-tert-Butyl-1-(2-cyclopentyl-ethyl)-4-hydroxy-2-oxo-2,5-dihydro-1H-pyrrol-3-yl]-2-cyano-1,1-dioxo-1,4-dihydro-1$\lambda^6$-benzo[1,4]thiazin-7-yl}-methanesulfonamide, N-{3-[(S)-5-tert-Butyl-1-(4-fluoro-3-methyl-benzyl)-4-hydroxy-2-oxo-2,5-dihydro-1H-pyrrol-3-yl]-2-fluoro-1,1-dioxo-1,4-dihydro-1$\lambda^6$-benzo[1,4]thiazin-7-yl}-methanesulfonamide, 3-[(S)-5-tert-Butyl-4-hydroxy-1-(3-methyl-butyl)-2-oxo-2,5-dihydro-1H-pyrrol-3-yl]-7-methanesulfonylamino-1,1-dioxo-1,4-dihydro-1$\lambda^6$-benzo[1,4]thiazine-2-carboxylic acid amide, 3-[(S)-5-tert-Butyl-1-(4-fluoro-benzyl)-4-hydroxy-2-oxo-2,5-dihydro-1H-pyrrol-3-yl]-7-methanesulfonylamino-1,1-dioxo-1,4-dihydro-1$\lambda^6$-benzo[1,4]thiazine-2-carboxylic acid amide, 3-[(S)-5-tert-Butyl-1-(4-fluoro-3-methyl-benzyl)-4-hydroxy-2-oxo-2,5-dihydro-1H-pyrrol-3-yl]-7-methanesulfonylamino-1,1-dioxo-1,4-dihydro-1$\lambda^6$-benzo[1,4]thiazine-2-carboxylic acid amide, N-{3-[(S)-5-tert-Butyl-4-hydroxy-1-(3-methyl-butyl)-2-oxo-2,5-dihydro-1H-pyrrol-3-yl]-2-methyl-1,1-dioxo-1,4-dihydro-1$\lambda^6$-benzo[1,4]thiazin-7-yl}-methanesulfonamide, or N-[(S)-3-tert-Butyl-2-(4-fluoro-benzyl)-1,5,6,6-tetraoxo-1,2,3,5,6,11-hexahydro-4-oxa-6$\lambda^6$-thia-2,11-diaza-cyclopenta[α]anthracen-8-yl]-methanesulfonamide (Ib, $R^2$=Me, $R^3$=tert-Bu, $R^4$=p-F-benzyl).

In another embodiment of the present invention there is provided a method for treating a disease caused by the Hepatitis C Virus (HCV) virus comprising administering to a patient in need thereof, a therapeutically effective quantity of a compound according to formula Ia or Ib wherein $R^1$, $R^2$, $R^3$, $R^4$, $R^5$, $R^a$, $R^b$, $R^c$, $R^d$, X and n are as defined herein above.

In another embodiment of the present invention there is provided a method for treating a disease caused by the Hepatitis C Virus (HCV) virus comprising co-administering to a patient in need thereof, a therapeutically effective quantity of a compound according to formula Ia or Ib wherein $R^1$, $R^2$, $R^3$, $R^4$, $R^5$, $R^a$, $R^b$, $R^c$, $R^d$, X and n are as defined herein above and at least one immune system modulator and/or at least one antiviral agent that inhibits replication of HCV.

In another embodiment of the present invention there is provided a method for treating a disease caused by the Hepatitis C Virus (HCV) virus comprising co-administering to a patient in need thereof, a therapeutically effective quantity of a compound according to formula Ia or Ib wherein $R^1$, $R^2$, $R^3$, $R^4$, $R^5$, $R^a$, $R^b$, $R^c$, $R^d$, X and n are as defined herein above and an immune system modulator which immune system modulator is immune system modulator is an interferon, interleukin, tumor necrosis factor or colony stimulating factor.

In another embodiment of the present invention there is provided a method for treating a disease caused by the Hepatitis C Virus (HCV) virus comprising co-administering to a patient in need thereof, a therapeutically effective quantity of a compound according to formula Ia or Ib wherein $R^1$, $R^2$, $R^3$, $R^4$, $R^5$, $R^a$, $R^b$, $R^c$, $R^d$, X and n are as defined herein above and an immune system modulator which immune system modulator is immune system modulator is interferon or chemically derivatized interferon.

In another embodiment of the present invention there is provided a method for treating a disease caused by the Hepatitis C Virus (HCV) virus comprising co-administering to a patient in need thereof, a therapeutically effective quantity of a compound according to formula Ia or Ib wherein $R^1$, $R^2$, $R^3$, $R^4$, $R^5$, $R^a$, $R^b$, $R^c$, $R^d$, X and n are as defined herein above and at least one other antiviral compound which antiviral compound(s) is(are) an HCV protease inhibitor, another HCV polymerase inhibitor, an HCV helicase inhibitor, an HCV primase inhibitor an HCV fusion inhibitor.

In another embodiment of the present invention there is provided a pharmaceutical composition according to formula Ia or Ib wherein $R^1$, $R^2$, $R^3$, $R^4$, $R^5$, $R^a$, $R^b$, $R^c$, $R^d$, X and n are as defined herein above and at least one pharmaceutically acceptable carrier, diluent or excipient.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition provided which generally is found in the Summary of the Invention.

The term "optional" or "optionally" as used herein means that a subsequently described event or circumstance may, but need not, occur, and that the description includes instances where the event or circumstance occurs and instances in which it does not. For example, "optionally substituted" means that the moiety may be hydrogen or a substituent.

The phrase "optional bond" means that the bond may or may not be present, and that the description includes single, double, or triple bonds. If a substituent is designated to be a "bond" or "absent", the atoms linked to the substituent are then directly connected.

The definitions described herein may be appended to form chemically-relevant combinations, such as "heteroalkylaryl," "haloalkylheteroaryl," "arylalkylheterocyclyl," "alkylcarbonyl," "alkoxyalkyl" and the like.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. One or more of the carbon atoms may optionally be replaced by oxygen, sulfur, substituted or unsubstituted nitrogen atom(s). Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"-, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl and 3-phenylpropyl. The terms "(het)arylalkyl" or "(het)aralkyl" are interpreted similarly except R' is optionally an aryl or a heteroaryl radical. The term "phenyl $C_{1-6}$ alkyl" refers to a radical R'R" wherein R' is a phenyl group and R" is an alkylene chain comprising 1 to 6 methylenes. An "alkylaminoalkyl" is an alkyl group having one to two alkylamino substituents(R' is alkylamino and R" is alkylene). "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl and so forth. Accordingly, as used herein, the term "hydroxyalkyl" is used to define a subset of heteroalkyl groups defined below.

The term "acyl" or "alkylcarbonyl" as used herein denotes a group of formula —C(=O)R wherein R is hydrogen or lower alkyl as defined herein. The term "arylcarbonyl" as used herein means a group of formula C(=O)R wherein R is an aryl group. The term "benzoyl" as used herein an "arylcarbonyl" group wherein R is phenyl.

The term "acylamino" as used herein denotes a group of formula —NHC(=O)R wherein R is hydrogen or lower alkyl as defined herein The term "alkenyl" as used herein denotes an unsubstituted hydrocarbon chain radical having from 2 to 10 carbon atoms having one or two olefinic double bonds. $C_{2-10}$ alkenyl" as used herein refers to an alkenyl composed of 2 to 10 carbons. Examples are vinyl, 1-propenyl, 2-propenyl(allyl) and 2-butenyl(crotyl).

The term "alkynyl" as used herein denotes an unbranched or branched hydrocarbon chain radical having from 2 to 10 carbon atoms, and having one or, where possible, two triple bonds. $C_{2-10}$ alkynyl" as used herein refers to an alkynyl composed of 2 to 10 carbons Examples are ethynyl, 1-propynyl, 2-propynyl, 1-butynyl, 2-butynyl or 3-butynyl.

The term "alkylene" as used herein denotes a divalent saturated linear hydrocarbon radical of 1 to 8 carbon atoms or a branched saturated divalent hydrocarbon radical of 3 to 8 carbon atoms, unless otherwise indicated. Examples of alkylene radicals include, but are not limited to, methylene, ethylene, propylene, 2-methyl-propylene, butylene, 2-ethylbutylene.

The term "cycloalkyl" as used herein denotes a saturated carbocyclic ring containing 3 to 7 carbon atoms, i.e. cyclopropyl, cyclobutyl, cyclopentyl, cyclohexyl or cycloheptyl. "$C_{3-7}$ cycloalkyl" as used herein refers to a cycloalkyl composed of 3 to 7 carbons in the carbocyclic ring.

The term "cycloalkyl-alkyl" as used herein refers to the radical R'R"-, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cycloalkyl and R" is $C_{1-3}$ alkylene as defined herein.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "aryl" as used herein denotes a monovalent aromatic carbocyclic radical containing 5 to 15 carbon atoms consisting of one individual ring, or one or more fused rings in which at least one ring is aromatic in nature, which can optionally be independently substituted with one or more, preferably one or three substituents. Examples of suitable substituents include, but are not limited to, hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylaminosulfonyl, arylaminosulfonyl, alkylsulfonylamino, arylsulfonylamino, carbamoyl, alkylcarbamoyl and dialkylcarbamoyl, arylcarbamoyl, alkylcarbonylamino and arylcarbonylamino, unless otherwise indicated. Alternatively two adjacent atoms of the aryl ring may be substituted with a methylenedioxy or ethylenedioxy group. Thus a bicyclic aryl substituents may be fused to a heterocyclyl or heteroaryl ring; however, the point of attachment of bicyclic aryl substituent is on the carbocyclic aromatic ring. Examples of aryl radicals include, but are not limited to, phenyl, naphthyl, indanyl, anthraquinolyl tetrahydronaphthyl, 3,4-methylenedioxyphenyl, 1,2,3,4-tetrahydroquinolin-7-yl and 1,2,3,4-tetrahydroisoquinoline-7-yl.

The term "aryloxy" as used herein denotes an O-aryl group, wherein aryl is as defined above. An aryloxy group can be unsubstituted or substituted with one or two suitable substituents. The term "phenoxy" refers to an aryloxy group wherein the aryl moiety is a phenyl ring.

The term "aryl-alkoxy" as used herein denotes an alkoxy group as defined herein wherein a hydrogen atom is replaced by an aryl is as defined above. An arylethoxy group is a 2-phenylethoxy or a 1-phenylalkoxy wherein the aryl ring is unsubstituted or substituted with one or two suitable substituents. The term "benzyloxy" refers to a phenylmethoxy group.

The term "heteroalkyl" as used herein means an alkyl radical as defined herein wherein one, two or three hydrogen atoms have been replaced with a substituent independently selected from the group consisting of —OR$^a$, —NR$^b$R$^c$C, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, alkylamino or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl. A hydroxyalkyl, aminoalkyl, (di)alkylaminoalkyl or thioalkyl group each represent distinct subsets of the heteroalkyl groups.

The term "heteroalkoxy" as used herein means an —O-(heteroalkyl) group wherein heteroalkyl is defined herein. C$_{1-10}$ heteroalkoxy" as used herein refers to an —O-(heteroalkyl) wherein alkyl is C$_{1-10}$. Representative examples include, but are not limited to, 2-dimethylaminoethoxy and 3-sulfonamido-1-propoxy.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on a heteroaryl ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heteroaryloxy" as used herein means an —O-heteroaryl group, wherein heteroaryl is as defined above such as 3-pyridyloxy and 2-pyrimidinyloxy.

The terms "hydroxyalkyl" and "alkoxyalkyl" as used herein denotes an alkyl group as defined herein where 1 to 3 hydrogens are replaced by a hydroxy radical or an alkoxy radical respectively and the attachment point of the hydroxyalkyl radical will be on the alkyl group.

The term "haloalkyl" as used herein denotes a unbranched or branched chain alkyl group as defined above wherein 1, 2, 3 or more hydrogen atoms are substituted by a halogen. "C$_{1-3}$ haloalkyl" as used herein refers to an haloalkyl composed of 1 to 3 carbons and 1-8 halogen substituents. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl and 2,2,2-trifluoroethyl.

The term "haloalkoxy" as used herein refers to a group —OR where R is haloalkyl as defined herein. The term "haloalkylthio" as used herein refers to a group —SR where R is haloalkyl as defined herein.

The term "halogen" or "halo" as used herein means fluorine, chlorine, bromine, or iodine.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds The term "combination" as used herein in reference to administering a plurality of drugs in a therapeutic regimen by concurrent or sequential administration of the drugs at the same time or at different times.

The term "chemically-derivatized interferon" as used herein refers to an interferon molecule covalently linked to a polymer which alters the physical and/or pharmacokinetic properties of the interferon. A non-limiting list of such polymers include polyalkylene oxide homopolymers such as polyethylene glycol (PEG) or polypropylene glycol (PPG), polyoxyethylenated polyols, copolymers thereof and block copolymers thereof, provided that the water solubility of the block copolymers is maintained. One skilled in the art will be aware of numerous approaches to linking the polymer and interferon (for example, see A. Kozlowski and J. M. Harris *J. Control. Release* 2001 72(1-3):217-24). A non-limiting list of chemically derivatized IFNα contemplated in the present patent includes PEG interferon-α-2a (PEGASYS®) and PEG interferon-α-2b (PEGINTRON®).

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "hydrate" as used herein means a compound of the invention or a salt thereof, that further includes a stoichiometric or non-stoichiometric amount of water bound by non-covalent intermolecular forces.

Commonly used abbreviations include: acetyl (Ac), azobis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride (BOC$_2$O), benzyl (Bn), butyl (Bu), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), (diphenylphosphino)ethane (dppe), (diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), acetic acid (HOAc), 1-N-hydroxybenzotriazole (HOBt), high pressure liquid chromatography (HPLC), lithium hexamethyl disilazane (LiHMDS), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-BuMe$_2$Si (TBDMS), triethylamine (TEA or Et$_3$N), triflate or CF$_3$SO$_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), 1,1'-bis-thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature of the R groups can varied as defined in the appended claims to afford the various compounds contemplated in this invention. Moreover, the reaction conditions are exemplary and alternative conditions can be identified without undue experimentation. The reaction sequences in the following examples are not meant to limit the scope of the invention as set forth in the claims.

SCHEME 1

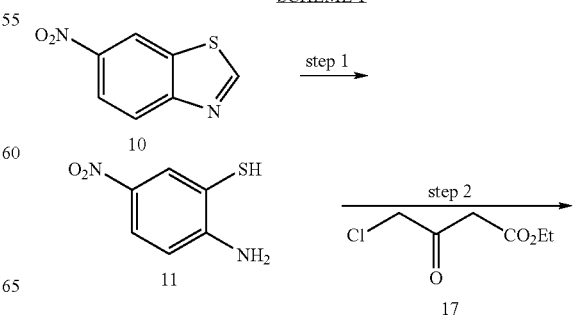

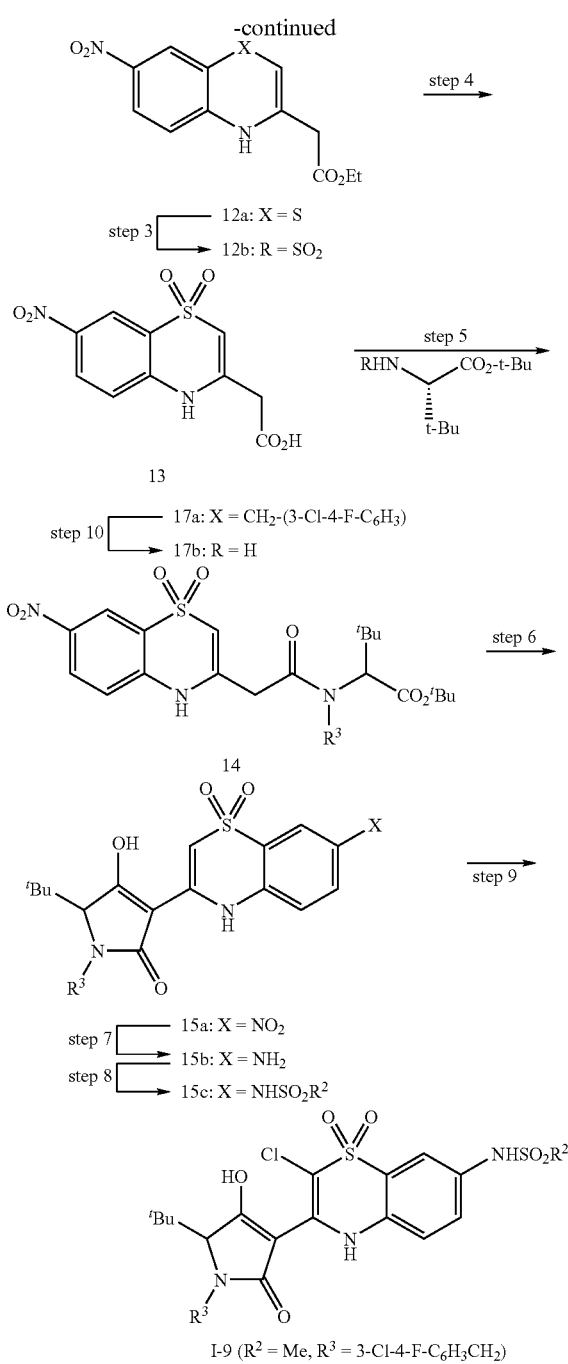

preferably at temperatures between 0 and 100° C. Cyclization of the intermediate aminoketone occurs spontaneously under the reaction condition to afford 12a. Oxidation of the sulfide to the corresponding sulfone (12a→12b) and hydrolysis of the ethyl ester (12b→13) were carried out using standard protocols to afford 13.

The construction of 4-hydroxy-1,5-dihydro-pyrrol-2-ones was accomplished by base-catalyzed intra-molecular cyclization of 2-(alkyl-(hetero)aryl-acetylamino)-alkanoic esters. The cyclization has been utilized for the solid phase synthesis of tetramic acids (J. Matthews and R. A. Rivero, *J. Org. Chem.* 1998 63(14):4808-4810). The requisite amides 14 were prepared by condensation of either 13 with an N-substituted α-amino acid ester 17a. One skilled in the art will appreciate that amino acids with a diverse substitution at the α-position are readily accessible and can be used to prepare compounds within the scope of the present invention.

Acylation of 17a is carried out by standard methodology. Such acylations are conveniently carried out with a corresponding acyl halide or acid anhydride in a solvent such as methylene chloride, chloroform, carbon tetrachloride, ether, THF, dioxane, benzene, toluene, MeCN, DMF, aqueous sodium hydroxide solution or sulfolane optionally in the presence of an inorganic or organic base at temperatures between −20 and 200° C., but preferably at temperatures between −10 and 160° C. Typical organic bases, e.g., tertiary amines, include but are not limited to TEA, DIPEA and pyridine. Typical inorganic bases include but are not limited to $K_2CO_3$ and $NaHCO_3$.

The acylation also may be carried out with the free carboxylic acid in the presence of an acid-activating agent or a dehydrating agent, e.g. isobutyl chloroformate; carbodiimides such as EDCI or DCC optionally in the presence of an additive such as HOBt, N-hydroxysuccinimide or TBTU in the presence of a base such as DIPEA or NMM; DCI or N,N'-thionyldiimidazole; or, $Ph_3P/CCl_4$ at temperatures between −20 and 200° C., but preferably at temperatures between −10 and 100° C.

The N-substituent on the pyrrolidone ring can be introduced by alkylation or reductive alkylation of 17b. These processes afford significant flexibility in the selection and introduction of an N-substituent. Reductive amination is preferably carried out carried out by combining an amine and carbonyl compound in the presence of a complex metal hydride such as sodium borohydride, lithium borohydride, sodium cyanoborohydride, zinc borohydride, sodium triacetoxyborohydride or borane/pyridine conveniently at a pH of 1-7 or, alternatively, with hydrogen in the presence of a hydrogenation catalyst, e.g. in the presence of palladium/charcoal, at a hydrogen pressure of 1 to 5 bar, preferably at temperatures between 20° C. and the boiling temperature of the solvent used. Optionally a dehydrating agent, such as molecular sieves or $Ti(IV)(O-i-Pr)_4$, is added to facilitate formation of the intermediate imine at ambient temperature. It may also be advantageous to protect potentially reactive groups during the reaction with conventional protecting groups which are cleaved again by conventional methods after the reaction. Reductive amination procedures have been reviewed: R. M. Hutchings and M. K. Hutchings *Reduction of C═N to CHNH by Metal Hydrides* in *Comprehensive Organic Synthesis* col. 8, I. Fleming (Ed) Pergamon, Oxford 1991 pp. 47-54.

(7-Nitro-1,1-dioxo-1,4-dihydro-1λ⁶-benzo[1,4]thiazin-3-yl)-acetic acid ethyl ester (12b) was prepared by alkylation and cyclization of 2-amino-5-nitro-thiophenol (11) and ethyl 3-chloroacetoacetate (17) to afford ethyl [4H-benzo[1,4]thiazin-(3E)-ylidene]-acetate (12a). The thiophenol 11 was prepared by unraveling 6-nitro-benzothiazole (10; CAS Reg. No. 2942-06-5). The alkylation of thiols and amines is optionally carried out in a solvent or mixture of solvents such as DCM, DMF, PhH, toluene, chlorobenzene, THF, PhH/THF, dioxane, MeCN or sulfolane with an alkylating agent such as an alkyl 3-chloroacetoacetate, optionally in the presence of a tertiary amine organic base or in the presence of an inorganic base, conveniently at temperatures between 0 and 150° C., Sodium tert-butoxide induced intramolecular cyclization of 14 affords the 4-hydroxy-1-(3-18 methyl-butyl)-1,5-dihydro-pyrrol-2-one (15a). While the cyclization is herein exemplified with sodium tert-butoxide, a variety of strong bases including potassium tert-butoxide, lithium diisopropyl amide (and other lithium dialkylamides), lithium hexamethyldisilazane and sodium hydride could be used interchangeably. The reaction is commonly carried out in ethereal solvents such as THF, dioxane or DME. Sodium or potassium alkoxides in alcoholic solvents can also be used in the cyclization. The reaction can be accomplished between −70 and 60° C.

Reduction of the nitro group (15a→15b) and sulfonation (15b→15c) were carried out by standard protocols. Numerous procedures are known for reduction of a nitro groups and one skilled in the art could readily choose appropriate conditions. The sulfonylation is carried out with the appropriate alkylsulfonyl chloride. Sulfonyl chlorides are commercially available or readily prepared by known procedures. Chlorination of the thiazine ring was accomplished with trifluoromethylsulfonyl chloride as the chlorinating agent. (G. H. Hakimelahi and G. Just, *Tetrahedron Lett.* 1979 3643-44)

Other substituents at the 2-position of the thiazine ring were introduced by electrophilic substitution analogous to the 2-chloro moiety. Reagents for electrophilic fluorination have been described (see, e.g., S. D. Taylor et al. *Tetrahedron* 1999 55:12431-12477) and treatment of the thiazine with N-fluorobenzenesulfonimide afforded the 2-fluoro compound. Thus the 2-methyl substituent was introduced by contacting the thiazine with formaldehyde in the presence of sodium cyanoborohydride under mildly acidic conditions. Under these conditions the intermediate hydroxymethyl compound is reduced by the hydride to the corresponding methyl substituent. One skilled in the art will recognize that the conditions would also be applicable to other carbonyl compounds sufficiently electrophilic to react with the thiazine ring. Sulfonyl cyanides, (e.g. p-toluenesulfonylcyanide) have two potentially electrophilic centers, the sulfur atom and the cyanide carbon atom in juxtaposition. In practice the cyanide carbon is more electrophilic and is subject to reaction with nucleophilic centers (see, e.g., A. M. van Leusen and J. C. Jagt, *Tetrahedron Lett.* 1970 12:967-970) and contacting the thiazine with p-toluenesulfonylcyanide affords the 2-cyano derivative which was hydrolyzed to the amide using standard procedures.

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. The following numbering system for these ring systems are as follows is shown in TABLE 1.

TABLE 1

(Ia)

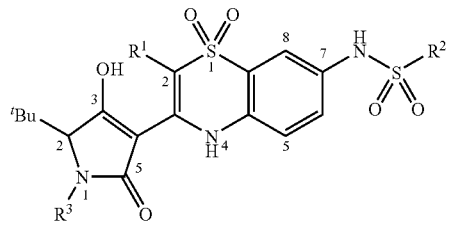

| Cpd No. | R¹ | R² | R³ | mw | mp (°C.) | ms |
|---|---|---|---|---|---|---|
| I-1 | Me | Me | CH$_2$-p-C$_6$H$_4$F | 549.64 | 170-174 | |
| I-2 | Cl | Me | iso-amyl | 532.08 | 142-145 | |
| I-3 | Cl | Me | CH$_2$-p-C$_6$H$_4$F | 570.06 | 144-148 | |
| I-4 | Cl | Et | CH$_2$-p-C$_6$H$_4$F | 584.09 | 136-140 | |
| I-5 | Cl | c-C$_3$H$_5$ | CH$_2$-p-C$_6$H$_4$F | 596.10 | 137-141 | |
| I-6 | Cl | Me | CH$_2$-4-F-3-Me-C$_6$H$_3$ | 584.09 | 140-146 | |
| I-7 | Cl | Et | CH$_2$-4-F-3-Me-C$_6$H$_3$ | 598.11 | 130-135 | |
| I-8 | Cl | c-C$_3$H$_5$ | CH$_2$-4-F-3-Me-C$_6$H$_3$ | 610.12 | 127-131 | |
| I-9 | Cl | Me | CH$_2$-3-Cl-4-F—C$_6$H$_3$ | 604.51 | 147-151 | |
| I-10 | Cl | Et | CH$_2$-3-Cl-4-F—C$_6$H$_3$ | 618.53 | 140-144 | |
| I-11 | Cl | c-C$_3$H$_5$ | CH$_2$-3-Cl-4-F—C$_6$H$_3$ | 630.54 | 137-141 | |
| I-12 | Cl | Et | iso-amyl | 546.11 | 125-165 | |
| I-13 | Cl | Me | 5-F-pyridin-2-ylmethyl | 571.05 | | 571.2 |
| I-14 | Cl | Me | CH$_2$Ph | 552.07 | 148-152 | |
| I-15 | Cl | Me | (CH$_2$)$_2$-c-C$_5$H$_9$ | 558.12 | 137-141 | |
| I-16 | Cl | Me | CH$_2$-4-F-3-MeO—C$_6$H$_3$ | 600.09 | 139-144 | |
| I-17 | Cl | Me | (CH$_2$)$_2$-c-C$_3$H$_5$ | 530.06 | | 530.1 |
| I-18 | F | Me | CH$_2$-4-F-3-Me-C$_6$H$_3$ | 567.63 | | 566.2 |
| I-19 | CN | Me | CH$_2$-p-C$_6$H$_4$F | 560.63 | | 559.2 |
| I-20 | —CONMe$_2$ | Me | CH$_2$-p-C$_6$H$_4$F | 606.69 | 140 | 605.1 |
| I-21 | —CONH$_2$ | Me | CH$_2$-p-C$_6$H$_4$F | 578.64 | | 579.0 |
| I-22 | —Cl | c-C$_3$H$_5$ | iso-amyl | 558.12 | | 558.1 556.1 |
| I-23 | —CN | Me | CH$_2$-4-F-3-Cl—C$_6$H$_3$ | 595.07 | | 595.1 |

TABLE 1-continued

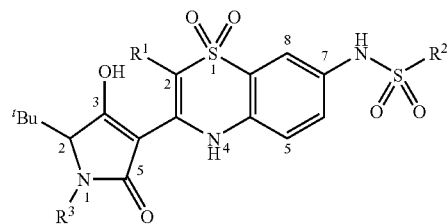

(Ia)

| Cpd No. | R¹ | R² | R³ | mw | mp (°C.) | ms |
|---|---|---|---|---|---|---|
| I-24 | —CN | Me | $CH_2$-4-F-3-MeO—$C_6H_3$ | 590.65 | 218 | 589.2 |
| I-25 | —CN | Me | $CH_2$-4-F-3-Me-$C_6H_3$ | 574.65 | >250 | 573.0 |
| I-26 | CN | Me | iso-amyl | 522.64 | >250 | 521.2 |
| I-27 | —CN | Me | $(CH_2)_2$-c-$C_3H_5$ | 520.63 | | 521.1 |
| I-28 | —CN | Me | $(CH_2)_2$-c-$C_5H_9$ | 548.68 | >250 | |
| I-29 | —$CONH_2$ | Me | iso-amyl | 540.66 | 150-155 | 541.1 |
| I-30 | —$CONH_2$ | Me | $CH_2$-4-F-3-Me-$C_6H_3$ | 592.67 | 168-172 | 593.0 |
| I-31 | Me | Me | iso-amyl | 511.66 | 210-215 | 510.2 |
| I-32 | | | | 561.61 | 120 | 560.2 |

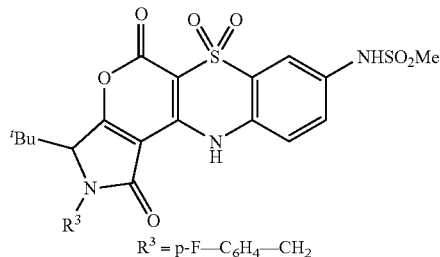

$R^3$ = p-F—$C_6H_4$—$CH_2$

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one).

Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor, an HCV protease inhibitor, interferon or a chemically-derivatized interferon. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

In general a therapeutically effective amount of a compound of the present invention, and optionally one or more additional antiviral agents, is an amount effective to reduce the viral load or achieve a sustained viral response to therapy. Useful indicators for a sustained response, in addition to the viral load include, but are not limited to liver fibrosis, elevation in serum transaminase levels and necroinflammatory activity in the liver. One common example, which is intended to be exemplary and not limiting, of a marker is serum alanine transaminase (ALT) which is measured by standard clinical assays. In some embodiments of the invention an effective treatment regimen is one which reduces ALT levels to less than about 45 IU/mL serum.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

EXAMPLE 1

N-{3-[(S)-5-tert-Butyl-1-(3-chloro-4-fluoro-benzyl)-4-hydroxy-2-oxo-2,5-dihydro-1H-pyrrol-3-yl]-2-chloro-1,1-dioxo-1,4-dihydro-1$\lambda^6$-benzo[1,4]thiazin-7-yl}-methanesulfonamide (I-9; see SCHEME 1)

steps 1 and 2—To a solution of 6-nitrobenzothiazole (10, 10.2 g, 57 mmol) in EtOH (500 mL) was added KOH (7.0 g, 125 mmol). The reaction was heated at reflux for 15 min then cooled to 0° C. Ethyl chloroacetoacetate (9.3 g, 57 mmol) was added and the mixture stirred at RT for 1 h. The reaction mixture was poured into 1N HCl (500 mL) and the resulting solid was collected. The solid was dissolved in EtOAc. The organic phase was washed with brine, dried (MgSO$_4$) and the solvent was removed under reduced pressure. The product was purified by SiO$_2$ chromatography eluting with 10% EtOAc/hexane to afford 0.61 g (70%) of 12a: LCMS RT 3.48 min, M+H.

step 3—To a solution of 12a (22 g, 81 mmol) in acetone (250 mL) and THF (50 mL) was added HCO$_2$H (37 g, 810 mmol). The mixture was cooled to 10° C. using an ice bath. KMnO$_4$ (32 g, 200 mmol) was slowly added with vigorous stirring. The reaction was allowed to warm to RT over two h with stirring. The solvent was removed under reduced pressure. Water (200 mL) and EtOAc (200 mL) were added. The mixture was filtered and the solid was washed with water and EtOAc. The filtrate and wash were combined and the organics were separated. The combined organic phases were washed with 1N HCl, saturated NaHCO$_3$ and brine. The organics were dried (MgSO$_4$) and the solvent was removed under reduced pressure. The residue was triturated with DCM and the resulting solid filtered to afford 8.3 g (34%) of 12b: LCMS RT 3.15 min, M+H.

step 4 To a suspension of 12b (3.0 g, 10 mmol) in MeOH (100 mL) was added 1N NaOH (100 mL). This mixture stirred at RT for 30 min. The MeOH was removed under reduced pressure and the residue was acidified by addition of 1N HCl. The solid was collected and washed with water and EtOAc to afford 2.4 g (8.5 mmol) of 13: LCMS RT 1.87 minutes.

step 5—To a solution of 13 (1.0 g, 3.5 mmol) and 17a (1.2 g, 3.5 mmol) in DMF (10 mL) was added DCC (0.44 g, 3.5 mmol). The reaction stirred at RT for 2 hours. 1N HCl (100 mL) was added and the resulting solid was collected. The solid was washed with water then dissolved in EtOAc. The EtOAc solution was washed with brine, dried (MgSO$_4$), and volatile solvent removed under reduced pressure to afford 2.1 g (3.5 mmol) of 14: LCMS RT 3.6 min, M–H.

step 6—A mixture of 14 (2.1 g, 3.5 mmol) and tert-BuONa (850 mg, 8.8 mmol) in EtOH (50 mL) was stirred at 60° C. for 4 h. The reaction was quenched by the addition of 1 N HCl until the mixture was acidic. The resulting solid was collected and washed with 1N HCl (50 mL). The solid was taken up in EtOAc (100 mL) and washed with brine. The organic layer was dried (MgSO$_4$) and the solvent was removed under reduced pressure to afford 1.8 g (100%) of 15a: LCMS RT 2.9 min, M–H step 7—A mixture of 15a (1.8 g, 3.5 mmol) was dissolved in EtOH (50 mL) and Pd/C (10% Degussa type, 250 mg) was added. The mixture was stirred vigorously under a balloon of H$_2$ for 6 h. The mixture was filtered through a CELITE® pad and the solvent was removed under reduced pressure. The product was purified by SiO$_2$ chromatography eluting with 5% EtOAc/DCM. The residue was triturated with DCM/Hexanes to afford 0.900 g (51%) of 15b: LCMS 2.9 min, M–H.

step 8—To a solution of 15b (150 mg, 0.30 mmol) in pyridine (5 mL) cooled to 0° C. was added methanesulfonyl chloride (69 mg, 0.60 mmol). After stirring at 0° C. for 30 min, 1N NaOH (30 mL) was added. The reaction stirred at RT for 30 min. The mixture was made acidic by addition of 1N HCl. The product was extracted into Et$_2$O. The combined organic phases were washed with brine and dried (MgSO$_4$). The product was purified by SiO$_2$ chromatography eluting 10% EtOAc/DCM to afford 0.110 g (63%) of 15c: LCMS 2.61 min, M–H.

step 9—To a solution of 15c (110 mg, 0.2 mmol) in pyridine (5 mL) cooled to 0° C. was added trifluoromethanesulfonyl chloride (29 mg, 0.17 mmol) as a 1M solution in DCE. After 1.5 min the reaction was quenched by adding 1N HCl until the reaction mixture was acidic. The product was extracted into EtOAc. The combined organic phases were washed with brine and dried (MgSO$_4$). The product was purified by SiO$_2$ chromatography eluting with 10% EtOAc/DCM to afford 44 mg (38%) of I-9: LCMS 3.67 min, M–H.

step 10—To a solution of O(t-Bu)-t-butylglycine HCl (17b, 2.0 g, 8.9 mmol) in DCM (90 mL) containing HOAc (10 mL) was added 3-chloro-4-fluoro-benzaldehyde (2.10 g, 13.4 mmol). This mixture stirred at RT for 18 h. The DCM was removed under reduced pressure. The residue was dissolved in EtOAc (100 mL) and was washed with 1N NaOH and brine. The organics were dried (MgSO$_4$) and removed under reduced pressure to afford 2.2 g (75%) of 17b: LCMS RT 3.13 min, M+H.

Ethanesulfonic acid {3-[(S)-5-tert-butyl-1-(3-chloro-4-fluoro-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-amide was prepared similarly except in step 8, methanesulfonyl chloride was replaced with ethanesulfonyl chloride to afford 32 mg (41%) of I-10: LCMS RT 3.78 min, M–H.

Cyclopropanesulfonic acid {3-[(S)-5-tert-butyl-1-(3-chloro-4-fluoro-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-amide was prepared similarly except in step 8, methanesulfonyl chloride was replaced with cyclopropanesulfonyl chloride to afford 52 mg (38%) of I-11: LCMS RT 3.80 min, M–H.

N-{3-[(S)-5-tert-Butyl-1-(4-fluoro-3-methyl-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-methanesulfonamide was prepared as described for I-9 except in step 10, 3-chloro-4-fluoro-benzaldehyde was replaced with 3-methyl-4-fluorobenzaldehyde to afford 58 mg (46%) of I-6: LCMS RT 3.66 min, M–H.

Ethanesulfonic acid {3-[(S)-5-tert-butyl-1-(3-chloro-4-fluoro-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-amide was prepared as described for I-6 except in step 8, methanesulfonyl chloride was replaced by ethanesulfonyl chloride to afford 48 mg (43%) of I-7: LCMS RT 3.61 min, M–H.

Cyclopropanesulfonic acid {3-[(S)-5-tert-butyl-1-(4-fluoro-3-methyl-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-amide was prepared as described for I-6 except in step 8, methanesulfonyl chloride was replaced by cyclopropylsulfonyl chloride to afford 48 mg (43%) of I-8: LCMS RT 3.61 min, M–H.

N-{3-[(S)-5-tert-Butyl-1-(4-fluoro-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-methanesulfonamide was prepared as described for I-9 except in step 10 3-chloro-4-fluorobenzaldehyde was replaced with 4-fluoro-benzaldehyde to afford 68 mg (46%) of I-3: LCMS RT 3.53 min, M–H.

Ethanesulfonic acid {3-[(S)-5-tert-butyl-1-(4-fluoro-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-amide was prepared as described for I-3 except in step 8, methanesulfonyl chloride was replaced by ethanesulfonyl chloride to afford 50 mg (47%) of I-4: LCMS RT 3.62 min, M–H.

Cyclopropanesulfonic acid {3-[(S)-5-tert-butyl-1-(4-fluoro-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-amide was prepared as described for I-3 except in step 8, methanesulfonyl chloride was replaced by cyclopropanesulfonyl chloride to afford 50 mg (47%) of I-5: LCMS RT 3.62 min, M–H.

N-{3-[(S)-5-tert-Butyl-4-hydroxy-1-(3-methyl-butyl)-2-oxo-2,5-dihydro-1H-pyrrol-3-yl]-2-chloro-1,1-dioxo-1,4-dihydro-1λ$^6$-benzo[1,4]thiazin-7-yl}-methanesulfonamide was prepared as described for I-9 except in step 10, 3-chloro-4-fluoro-benzaldehyde was replaced with 3-methyl-butanal to afford 40 mg (29%) of I-2: LCMS RT 3.99 min, M+H.

Ethanesulfonic acid {3-[(S)-5-tert-butyl-4-hydroxy-1-(3-methyl-butyl)-2-oxo-2,5-dihydro-1H-pyrrol-3-yl]-2-chloro-1,1-dioxo-1,4-dihydro-1λ$^6$-benzo[1,4]thiazin-7-yl}-amide was prepared as described for I-2 except in step 8, methanesulfonyl chloride was replaced by ethanesulfonyl chloride to afford 23 mg (22%) of I-12: LCMS RT 3.82 min, M–H.

Cyclopropanesulfonic acid {3-[(S)-5-tert-butyl-4-hydroxy-1-(3-methyl-butyl)-2-oxo-2,5-dihydro-1H-pyrrol-3-yl]-2-chloro-1,1-dioxo-1,4-dihydro-1λ$^6$-benzo[1,4]thiazin-7-yl}-amide was prepared as described for I-2 except in step 8, methanesulfonyl chloride was replaced by cyclopropanesulfonic acid to afford 40 mg (33%) of I-22: LCMS RT 3.87 min, M–H.

N-{3-[(S)-5-tert-Butyl-1-(2-cyclopentyl-ethyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-methanesulfonamide was prepared as described for I-9 except in step 10 3-chloro-4-fluorobenzaldehyde was replaced with cyclopentylacetaldehyde to afford 65 mg (38%) of I-15: LCMS RT 3.96 min, M–H.

N-[3-((S)-1-Benzyl-5-tert-butyl-4-hydroxy-2-oxo-2,5-dihydro-1H-pyrrol-3-yl)-2-chloro-1,1-dioxo-1,4-dihydro-1λ$^6$-benzo[1,4]thiazin-7-yl]-methanesulfonamide was prepared as described for I-9 except in step 10 3-chloro-4-fluorobenzaldehyde was replaced with benzaldehyde to afford 44 mg (21%) of I-14: LCMS RT 3.52 min, M–H.

N-{3-[(S)-5-tert-Butyl-1-(4-fluoro-3-methoxy-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-methanesulfonamide was prepared as described for I-9 except in step 10 3-chloro-4-fluorobenzaldehyde was replaced with 4-fluoro-3-methoxybenzaldehyde to afford 44 mg (36%) of I-16: LCMS RT 3.41 min, M–H.

5-tert-Butyl-1-(5-fluoro-pyridin-2-ylmethyl)-4-hydroxy-3-(7-methanesulfonyl-1,1-dioxo-1,4-dihydro-1λ$^6$-benzo[1,4]thiazin-3-yl)-1,5-dihydro-pyrrol-2-one was prepared as described for I-9 except in step 10, 3-chloro-4-fluorobenzaldehyde was replaced with 5-fluoropicolinaldehyde to afford 80 mg (47%) of I-13: LCMS RT 3.45 min, M+H.

EXAMPLE 2

5-tert-Butyl-1-(4-fluoro-benzyl)-4-hydroxy-3-(7-methanesulfonyl-2-methyl-1,1-dioxo-1,4-dihydro-1λ⁶-benzo[1,4]thiazin-3-yl)-1,5-dihydro-pyrrol-2-one (I-1)

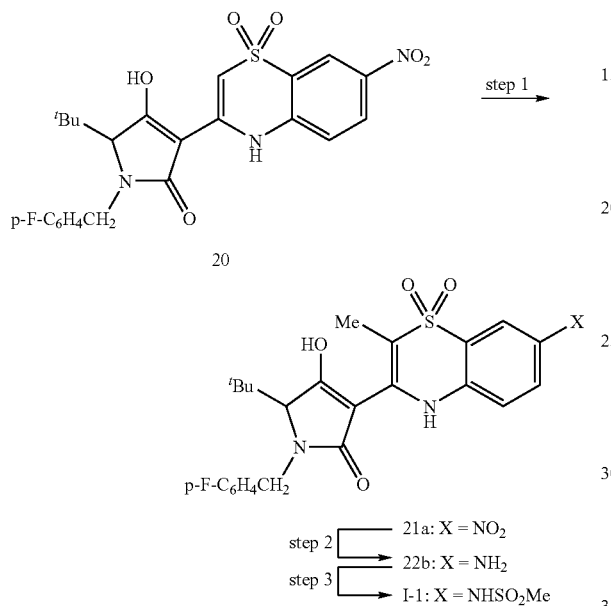

5-tert-Butyl-1-(4-fluoro-benzyl)-4-hydroxy-3-(7-nitro-1,1-dioxo-1,4-dihydro-1λ⁶-benzo[1,4]thiazin-3-yl)-1,5-dihydro-pyrrol-2-one (20) was prepared by the sequence used to prepare 15a (SCHEME 1, steps 1-6 and 10) except in step 10, 3-chloro-4-fluoro-benzaldehyde was replaced with 4-fluorobenzaldehyde.

step 1—To a solution of 20 (0.42 g, 0.86 mmol) and formaldehyde (37% in water, 0.70 g, 8.6 mmol) in MeCN (50 mL) was added sodium cyanoborohydride (0.27 g, 4.3 mmol). This mixture stirred at RT for 15 min. HOAc was added dropwise to adjust the pH to 4. After 15 min 1N HCl (20 mL) was added and the mixture stirred for 30 min. Brine (50 mL) was added and the product was extracted into ether. The combined extracts were dried (MgSO₄) and the solvent was removed under reduced pressure. The product was purified by SiO₂ chromatography eluting with DCM then 5% EtOAc/DCM to afford 175 mg (41%) of 21a: LCMS RT 3.16 min, M–H.

step 2—A mixture of 21a (0.175 g, 0.35 mmol), EtOH (50 mL) and Raney nickel (slurry, 1 mL) was stirred vigorously under a balloon of H₂ for 2 h. The mixture was filtered through a CELITE® pad and the solvent was removed under reduced pressure. The product was purified by SiO₂ chromatography eluting with 5% EtOAc/DCM. The eluant was triturated with DCM/hexanes to afford 80 mg (48%) of 22b: LCMS 3.7 min, M+H.

step 3—To a 0° C. solution of 22b (80 mg, 0.17 mmol) in pyridine (5 mL) was added methanesulfonylchloride (39 mg, 0.34 mmol). After stirring at 0° C. for 30 min, 1N NaOH (30 mL) was added. The reaction stirred at RT for 30 min. 1N HCl was added until the mixture was acidic. The product was extracted into Et₂O. The organics were washed with brine and dried (MgSO₄). The product was purified by SiO₂ chromatography eluting with 10% EtOAc/DCM to afford 67 mg (72%) of I-1: LCMS 2.11 min, M–H.

EXAMPLE 3

N-[3-(5-tert-Butyl-4-hydroxy-1-isobutyl-2-oxo-2,5-dihydro-1H-pyrrol-3-yl)-2-methyl-1,1-dioxo-1,4-dihydro-1λ⁶-benzo[1,4]thiazin-7-yl]-methanesulfonamide (I-31)

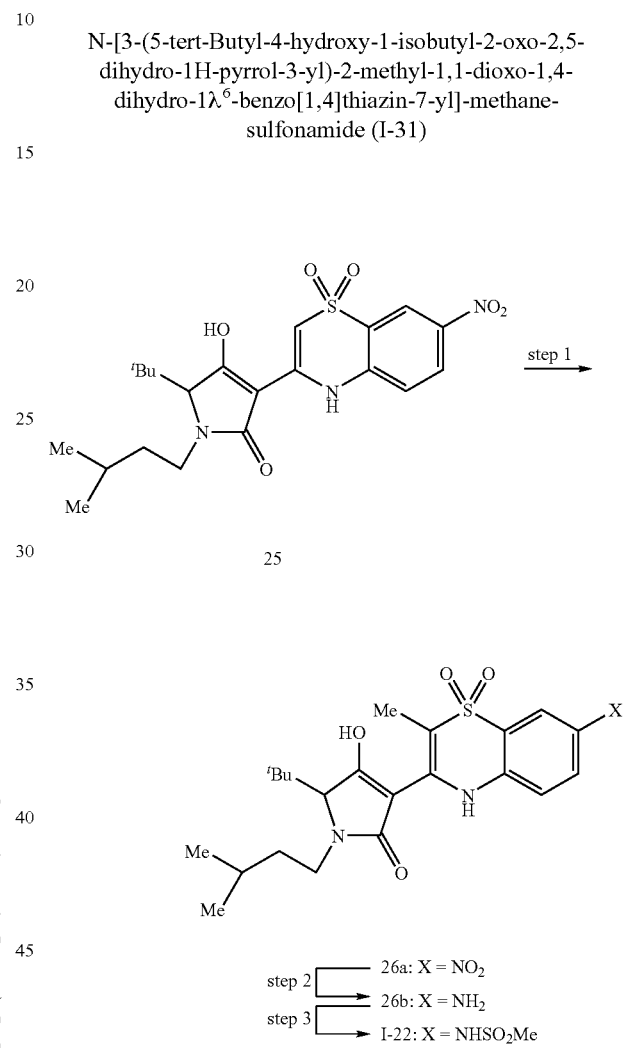

5-tert-Butyl-1-isobutyl-4-methyl-3-(2-methyl-7-nitro-1,1-dioxo-1,4-dihydro-1λ⁶-benzo[1,4]thiazin-3-yl)-1,5-dihydro-pyrrol-2-one (25) was prepared by the sequence used to prepare 15a (SCHEME 1, steps 1-6 and 10) except in step 10, 3-chloro-4-fluoro-benzaldehyde was replaced with 3-methylbutanal.

N-[3-(5-tert-Butyl-1-isobutyl-4-methyl-2-oxo-2,5-dihydro-1H-pyrrol-3-yl)-2-methyl-1,1-dioxo-1,4-dihydro-1λ⁶-benzo[1,4]thiazin-7-yl]-methanesulfonamide was prepared as described for I-1 (Example 2) except in step 1 20 was replaced with 25 to afford 30 mg (32%) of I-31: LCMS RT 4.37 min, M+H.

EXAMPLE 4

N-{3-[(S)-5-tert-Butyl-1-(4-fluoro-3-methyl-benzyl)-4-hydroxy-2-oxo-2,5-dihydro-1H-pyrrol-3-yl]-2-fluoro-1,1-dioxo-1,4-dihydro-1λ$^6$-benzo[1,4]thiazin-7-yl}-methanesulfonamide (I-18)

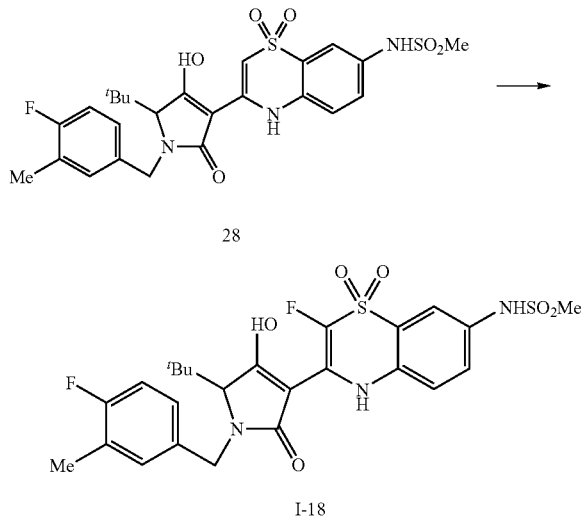

To a solution of 28 (100 mg, 0.182 mmol) in DCM (2 mL) and EtOH (1 mL) was added K$_2$CO$_3$ (126 mg, 0.91 mmol) and N-fluorobenzenesulfonimide (57 mg, 0.182 mmol). This mixture was stirred at RT for 1 h. The mixture was acidified with 1N HCl and the resulting mixture was extracted into EtOAc. The combined extracts were washed with brine, dried (MgSO$_4$), filtered and evaporated in vacuo. The product was purified by SiO$_2$ chromatography eluting with 5% EtOAc/DCM to afford 11 mg (11%) of I-18: LCMS RT 3.64 min, M−H.

EXAMPLE 5

N-{3-[5-tert-Butyl-1-(3-chloro-4-fluoro-benzyl)-4-hydroxy-2-oxo-2,5-dihydro-1H-pyrrol-3-yl]-2-cyano-1,1-dioxo-1,4-dihydro-1λ$^6$-benzo[1,4]thiazin-7-yl}-methanesulfonamide (I-23)

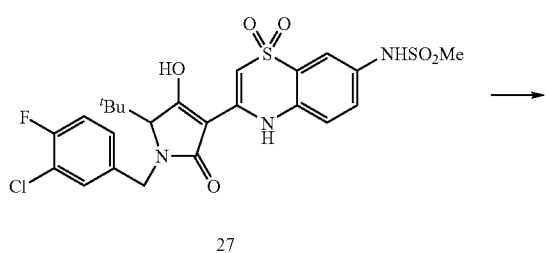

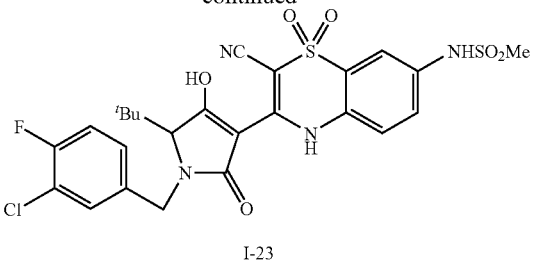

2-Cyano substituted thiazines were prepared utilizing the corresponding thiazine unsubstituted at the 2-position. These precursors were prepared as depicted in SCHEME 1 and exemplified in example 1 except step 9 is omitted. The appropriate N-pyrrolidone substituent is introduced by using the appropriate aldehyde in the reductive amination in step 10 of example 1.

To a solution of 27 (190 mg, 0.33 mmol) in pyridine (5 mL) cooled to 0° C. was added p-toluenesulfonyl cyanide (90 mg, 0.50 mmol). The reaction mixture was stirred at 0° C. for 1 h. A saturated solution of NaHCO$_3$ (50 mL) was added and the resulting mixture was thrice extracted with EtOAc (3×50 mL). The combined extracts were washed with brine, dried (MgSO$_4$), filtered and evaporated in vacuo. The crude product was purified by SiO$_2$ chromatography eluting with 5% MeOH/DCM to afford 66 mg (33%) of I-23: LCMS RT 2.64 min, M+H.

N-{3-[5-tert-Butyl-1-(4-fluoro-3-methoxy-benzyl)-4-hydroxy-2-oxo-2,5-dihydro-1H-pyrrol-3-yl]-2-cyano-1,1-dioxo-1,4-dihydro-1λ$^6$-benzo[1,4]thiazin-7-yl}-methanesulfonamide was prepared analogously from N-{3-[5-tert-butyl-1-(4-fluoro-3-methoxy-benzyl)-4-hydroxy-2-oxo-2,5-dihydro-1H-pyrrol-3-yl]-1,1-dioxo-1,4-dihydro-1λ$^6$-benzo[1,4]thiazin-7-yl}-methanesulfonamide (15c, R$^3$=4-F-3-MeO—C$_6$H$_3$CH$_2$) to afford 35 mg (24%) of I-24: LCMS RT 2.51 min, M−H.

N-{3-[5-tert-Butyl-1-(4-fluoro-benzyl)-4-hydroxy-2-oxo-2,5-dihydro-1H-pyrrol-3-yl]-2-cyano-1,1-dioxo-1,4-dihydro-1λ$^6$-benzo[1,4]thiazin-7-yl}-methanesulfonamide was prepared analogously from N-{3-[5-tert-butyl-1-(4-fluoro-benzyl)-4-hydroxy-2-oxo-2,5-dihydro-1H-pyrrol-3-yl]-1,1-dioxo-1,4-dihydro-1λ$^6$-benzo[1,4]thiazin-7-yl}-methanesulfonamide (15c, R$^3$=4-F—C$_6$H$_4$—CH$_2$) to afford 80 mg (59%) of I-19: LCMS RT 2.42 min, M−H.

N-{3-[5-tert-Butyl-1-(4-fluoro-3-methyl-benzyl)-4-hydroxy-2-oxo-2,5-dihydro-1H-pyrrol-3-yl]-2-cyano-1,1-dioxo-1,4-dihydro-1λ$^6$-benzo[1,4]thiazin-7-yl}-methanesulfonamide was prepared from N-{3-[5-tert-butyl-1-(4-fluoro-3-methyl-benzyl)-4-hydroxy-2-oxo-2,5-dihydro-1H-pyrrol-3-yl]-1,1-dioxo-1,4-dihydro-1λ$^6$-benzo[1,4]thiazin-7-yl}-methanesulfonamide (15c, R$^3$=4-F-3-Me—C$_6$H$_3$CH$_2$) to afford 14 mg (13%) of I-25: LCMS RT 3.44 min, M+H.

N-{3-[5-tert-Butyl-4-hydroxy-1-(3-methyl-butyl)-2-oxo-2,5-dihydro-1H-pyrrol-3-yl]-2-cyano-1,1-dioxo-1,4-dihydro-1λ$^6$-benzo[1,4]thiazin-7-yl}-methanesulfonamide was prepared from N-{3-[5-tert-butyl-4-hydroxy-1-(3-methyl-butyl)-2-oxo-2,5-dihydro-1H-pyrrol-3-yl]-1,1-dioxo-1,4-dihydro-1λ$^6$-benzo[1,4]thiazin-7-yl}-methanesulfonamide (15c, R$^3$=Me$_2$CH(CH$_2$)$_2$) to afford 28 mg (27%) of I-26: LCMS RT 2.48 min, M−H.

N-{3-[5-tert-Butyl-1-(2-cyclopropyl-ethyl)-4-hydroxy-2-oxo-2,5-dihydro-1H-pyrrol-3-yl]-2-cyano-1,1-dioxo-1,4-dihydro-1λ$^6$-benzo[1,4]thiazin-7-yl}-methanesulfonamide was prepared from N-{3-[5-tert-butyl-1-(2-cyclopropyl-ethyl)-4-hydroxy-2-oxo-2,5-dihydro-1H-pyrrol-3-yl]-1,1-dioxo-1,4-dihydro-1λ$^6$-benzo[1,4]thiazin-7-yl}-methane-sulfonamide (15c, R$^3$=c-C$_3$H$_5$—(CH$_2$)$_2$) to afford 78 mg (49%) of I-27: LCMS RT 2.40 min, M+H.

N-{3-[5-tert-Butyl-1-(2-cyclopentyl-ethyl)-4-hydroxy-2-oxo-2,5-dihydro-1H-pyrrol-3-yl]-2-cyano-1,1-dioxo-1,4-dihydro-1λ$^6$-benzo[1,4]thiazin-7-yl}-methanesulfonamide was prepared from N-{3-[5-tert-butyl-1-(2-cyclopentyl-ethyl)-4-hydroxy-2-oxo-2,5-dihydro-1H-pyrrol-3-yl]-1,1-dioxo-1,4-dihydro-1λ$^6$-benzo[1,4]thiazin-7-yl}-methane-sulfonamide (15c, R$^3$=c-C$_5$H$_9$—(CH$_2$)$_2$) to afford 27 mg (16%) of I-28: LCMS RT 2.71 min, M−H.

EXAMPLE 6

3-[(S)-5-tert-Butyl-4-hydroxy-1-(3-methyl-butyl)-2-oxo-2,5-dihydro-1H-pyrrol-3-yl]-7-methanesulfony-lamino-1,1-dioxo-1,4-dihydro-1λ$^6$-benzo[1,4]thiaz-ine-2-carboxylic acid amide (I-29)

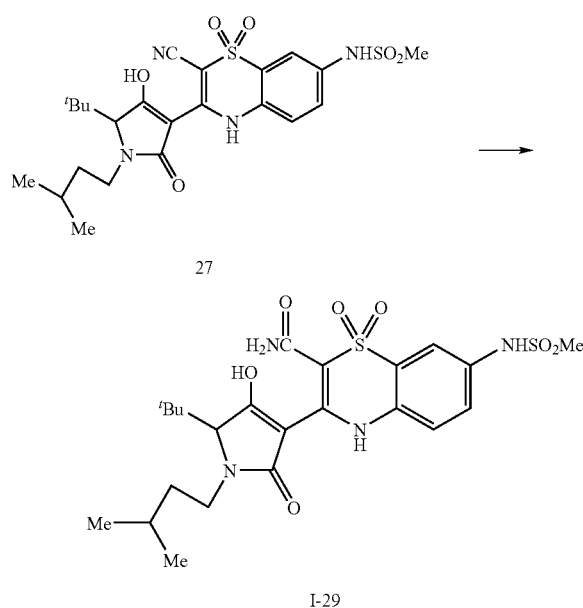

A solution of I-26 (217 mg, 0.40 mmol), 1N HCl (50 mL) and THF (10 mL) was stirred at RT for 30 min. EtOAc (50 mL) was added and the organic phase was separated. The organic phase was washed with brine, dried (MgSO$_4$), filtered and evaporated in vacuo. The product was purified by SiO$_2$ chromatography eluting with 2.5% MeOH/DCM to afford 32 mg (15%) of I-29: LCMS RT 3.40 min, M+H.

3-[(S)-5-tert-Butyl-1-(4-fluoro-benzyl)-4-methoxy-2-oxo-2,5-dihydro-1H-pyrrol-3-yl]-7-methanesulfonylamino-1,1-dioxo-1,4-dihydro-1λ$^6$-benzo[1,4]thiazine-2-carboxylic acid amide was prepared analogously from I-19 to afford 15 mg (29%) of I-21: LCMS RT 3.30 min, M+H.

3-[(S)-5-tert-Butyl-1-(4-fluoro-3-methyl-benzyl)-4-hydroxy-2-oxo-2,5-dihydro-1H-pyrrol-3-yl]-7-methanesulfo-nylamino-1,1-dioxo-1,4-dihydro-1λ$^6$-benzo[1,4]thiazine-2-carboxylic acid amide was prepared analogously from I-26 to afford 14 mg (13%) of I-30: LCMS RT 3.44 min, M+H.

EXAMPLE 7

N-[(S)-3-tert-Butyl-2-(4-fluoro-benzyl)-1,5,6,6-tet-raoxo-1,2,3,5,6,11-hexahydro-4-oxa-6λ$^6$-thia-2,11-diaza-cyclopenta[a]anthracen-8-yl]-methanesulfona-mide (I-32)

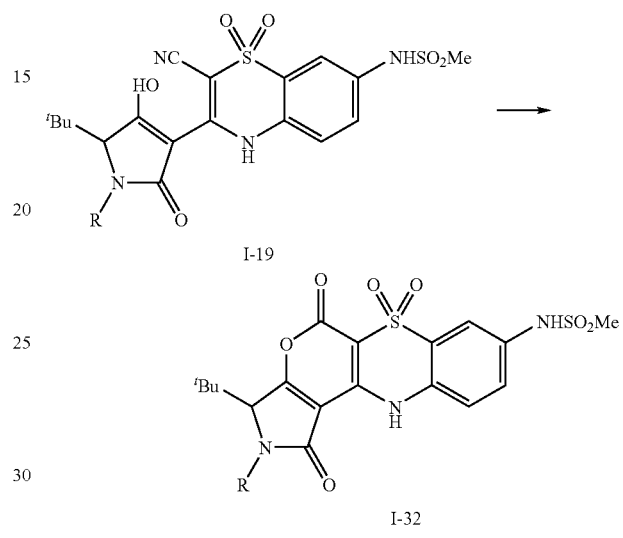

R = p-F—C$_6$H$_4$—CH$_2$

To a solution of I-19 (200 mg, 0.357 mmol) in THF (4 mL) and water (4 mL) was added 6M HCl (0.2 mL). The mixture was heated to 50° C. for 15 h, cooled to RT and a saturated NaHCO$_3$ was added to neutralize the acid. The product was extracted into DCM. The organics extracts were washed with brine and dried (MgSO$_4$), filtered and evaporated in vacuo. The crude product was triturated with DCM to afford 160 mg (80%) of I-32: LCMS RT 3.04 min. M−H.

EXAMPLE 8

HCV NS5B RNA Polymerase Activity

The enzymatic activity of HCV NS5B570n-BK is measured as incorporation of radiolabeled nucleotide monophosphates into acid insoluble RNA products. Unincorporated radiolabel substrate is removed by filtration and scintillant is added to the washed and dried filter plate containing radiolabeled RNA product. The light emitted by the scintillant is proportional to the amount of RNA product generated by NS5B570n-BK at the endpoint of the reaction.

The N-terminally histidine tagged HCV polymerase, derived from HCV BK strain, genotype 1b (NS5B570n-BK) contains a 21 amino acid deletion at the C-terminus relative to the full-length HCV polymerase and is purified from E. coli strain M15. The construct containing the coding sequence of HCV BK strain amino acid residues 2421-2999 (GenBank accession number M58335) downstream of a Taq promoter expression cassette was inserted into plasmid constructs. The plasmid constructs are transformed in E. coli and colonies are inoculated and grown overnight in 10 L of Terrific broth (Tartoff and Hobbs) supplemented with 100 μg/mL ampicillin at 37° C. Protein expression is induced by addition of 1 mM isopropyl-β-D-thiogalactopyranoside (IPTG), when optical densities reaches between 1.5 and 3.5 $OD_{600}$ and the culture is then incubated for 16- to 18 h at 22° C. NS5B570n-BK is purified to homogeneity using a three step protocol including subsequent column chromatography on Ni-NTA, SP-Sepharose HP and Superdex 75 resins.

Each 50 μL enzymatic reaction contains 8:4 μg/mL poly A:oligo $U_{16}$ (template:primer), 200 nM NS5B570n-BK enzyme, 2.1 μCi of tritiated UTP (Perkin Elmer catalog no. TRK-412; specific activity: 30 to 60 Ci/mmol; stock solution concentration from $7.5 \times 10^{-5}$ M to $20.6 \times 10^{-6}$ M), 1 μM ATP, CTP, and GTP, 40 mM Tris-HCl pH 8.0, 2 to 40 mM NaCl, 4 mM DTT (dithiothreitol), 4 mM $MgCl_2$, and 5 μL of compound serial diluted in DMSO. Reaction mixtures are assembled in MADVN0B 96-well filter plates (Millipore Co.) and incubated for 2 h at 30° C. Reactions are stopped by addition of 10% (v/v) trichloroacetic acid and incubated for 40 min at 4° C. Reactions are filtered, washed with 6 reaction volumes of 10% (v/v) trichloroacetic acetic acid, 2 reaction volumes of 70% (v/v) ethanol, air dried, and 25 μL of scintillant (Microscint 20, Perkin-Elmer) is added to each reaction well.

The amount of light emitted from the scintillant is converted to counts per minute (CPM) on a Topcount® plate reader (Perkin-Elmer, Energy Range: Low, Efficiency Mode: Normal, Count Time: 1 min, Background Subtract: none, Cross talk reduction: Off).

Data is analyzed with GraphPad® Prism® and/or Microsoft® Excel®. The reaction in the absence of enzyme is used to determine the background signal, which is subtracted from the enzymatic reactions. Positive control reactions are performed in the absence of compound, from which the background corrected activity is set as 100% polymerase activity. All data is expressed as a percentage of the positive control. The compound concentration at which the enzyme-catalyzed rate of RNA synthesis is reduced by 50% ($IC_{50}$) is calculated by fitting equation (i) to $$Y = \% \text{ Min} + \frac{(\% \text{ Max} - \% \text{ Min})}{\left[1 + \frac{X}{(IC_{50})^S}\right]} \quad (i)$$

the data, where "Y" corresponds to the relative enzyme activity (in %), "% Min" is the residual relative enzymatic activity at saturating compound concentration, "% Max" is the maximal relative enzymatic activity compared to positive control, X corresponds to the compound concentration, and "S" is the Hill coefficient (or slope). Representative data is in TABLE 2 (infra).

EXAMPLE 9

*Renilla luciferase* Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla luciferase* gene was introduced into the first open reading frame of a replicon construct NK5.1 (N. Krieger et al., *J. Virol.* 2001 75(10): 4614), immediately after the internal ribosome entry site (IRES) sequence, and fused with the neomycin phosphotransferase (NPTII) gene via a self-cleavage peptide 2A from foot and mouth disease virus (Ryan & Drew, EMBO Vol 13:928-933). After in vitro transcription the RNA was electroporated into human hepatoma Huh7 cells, and G418-resistant colonies were isolated and expanded. Stably selected cell line 2209-23 contains replicative HCV subgenomic RNA, and the activity of *Renilla luciferase* expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation.

*Renilla luciferase* HCV replicon cells (2209-23) cultured in Dulbecco's MEM (GibcoBRL cat no. 31966-021) with 5% fetal calf serum (FCS, GibcoBRL cat. no. 10106-169) were plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using Dual-Luciferase reporter assay system (Promega cat no. E1960). All the reagents described in the following paragraph were included in the manufacturer's kit, and the manufacturer's instructions were followed for preparations of the reagents. The cells were washed twice with 200 μl of phosphate buffered saline (pH 7.0) (PBS) per well and lysed with 25 μl of 1× passive lysis buffer prior to incubation at room temperature for 20 min. One hundred microliter of LAR II reagent was added to each well. The plate was then inserted into the LB 96V microplate luminometer (MicroLumatPlus, Berthold), and 100 μl of Stop & Glo® reagent was injected into each well and the signal measured using a 2-second delay, 10-second measurement program. $IC_{50}$, the concentration of the drug required for reducing replicon level by 50% in relation to the untreated cell control value, can be calculated from the plot of percentage reduction of the luciferase activity vs. drug concentration.

WST-1 reagent from Roche Diagnostic (cat no. 1644807) was used for the cytotoxicity assay. Ten microliter of WST-1 reagent was added to each well including wells that contain media alone as blanks. Cells were then incubated for 1 to 1.5 hours at 37° C., and the OD value was measured by a 96-well plate reader at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration.

TABLE 2

| Compound Number | Polymerase Assay $IC_{50}$ (μM) | R. luciferase Activity $IC_{50}$ (μM) |
| --- | --- | --- |
| I-3 | 0.002 | 0.004 |
| I-18 | 0.005 | 0.016 |
| I-19 | 0.006 | 0.016 |

EXAMPLE 10

Pharmaceutical compositions of the subject Compounds for administration via several routes were prepared as described in this Example.

| Composition for Oral Administration (A) | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
| --- | --- |
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

The ingredients are mixed to form a suspension for oral administration.

| Parenteral Formulation (D) | |
| --- | --- |
| Ingredient | % wt./wt. |
| Active ingredient | 0.25 g |
| Sodium Chloride | q.s. to make isotonic |
| Water for injection to | 100 mL |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound according to formula Ia wherein:

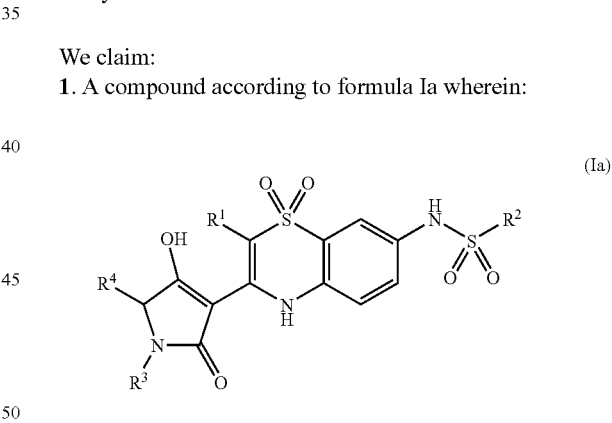

(Ia)

$R^1$ is halogen, $C_{1-3}$ alkyl, $COR^5$, $CH_2COR^5$, CN or $CH_2CN$;

$R^2$ is $C_{1-6}$ alkyl, $C_{3-7}$ cycloalkyl, $C_{3-7}$ cycloalkyl-$C_{1-3}$ alkyl, phenyl-$C_{1-3}$ alkyl, $NR^aR^b$ or phenyl wherein said phenyl rings are optionally substituted with 1 to 3 groups independently selected in each occurrence from the group consisting of $C_{1-6}$ alkyl, $C_{1-6}$ alkoxy, halogen, $NR^aR^b$ and cyano;

$R^3$ is $C_{1-6}$ alkyl, $C_{3-7}$ cycloalkyl-$C_{1-3}$ alkyl, phenyl-$C_{1-3}$ alkyl wherein said phenyl is optionally substituted with 1 to 3 groups independently selected in each occurrence from the group consisting of $C_{1-6}$ alkyl, $C_{1-6}$ alkoxy, halogen, $NR^aR^b$, nitro and cyano, or pyridinyl-methyl said pyridinyl optionally substituted with halogen;

$R^4$ is $C_{1-6}$ alkyl or $C_{3-7}$ cycloalkyl;

$R^5$ is OH, $C_{1-6}$ alkoxy, $NR^cR^d$;

R$^a$ and R$^b$ (i) taken independently in each occurrence are hydrogen or C$_{1-6}$ alkyl or (ii) taken together are (CH$_2$)$_n$ wherein n is 4-6 or (CH$_2$)$_2$X(CH$_2$)$_2$ wherein X is O, S, NR$^c$;

R$^c$ and R$^d$ are independently hydrogen or C$_{1-6}$ alkyl; or, pharmaceutically acceptable salts thereof.

2. A compound according to claim 1 wherein:
R$^1$ is halogen;
R$^2$ is C$_{1-6}$ alkyl or C$_{3-7}$ cycloalkyl;
R$^3$ is C$_{1-6}$ alkyl; C$_{3-7}$ cycloalkyl-C$_{1-3}$ alkyl or phenyl C$_{1-3}$ alkyl wherein said phenyl is optionally substituted with 1 to 3 groups independently selected in each occurrence from the group consisting of C$_{1-6}$ alkyl, C$_{1-6}$ alkoxy, halogen, NR$^a$R$^b$, nitro and cyano;
R$^4$ is C$_{1-6}$ alkyl.

3. A compound according to claim 2 wherein R$^3$ is C$_{1-6}$ alkyl or phenyl-C$_{1-3}$ alkyl wherein said phenyl is optionally substituted with 1 to 3 groups independently selected in each occurrence from the group consisting of C$_{1-6}$ alkyl, halogen and C$_{1-6}$ alkoxy.

4. A compound according to claim 3 wherein R$^2$ is C$_{1-6}$ alkyl.

5. A compound according to claim 1 wherein said compound is of formula Ia and R$^1$ is chloro.

6. A compound according to claim 1 wherein said compound is of formula Ia and:
R$^1$ is halogen;
R$^2$ is NR$^a$R$^b$;
R$^3$ is C$_{1-6}$ alkyl; C$_{3-7}$ cycloalkyl-C$_{1-3}$ alkyl or phenyl-C$_{1-3}$ alkyl wherein said phenyl is optionally substituted with 1 to 3 groups independently selected in each occurrence from the group consisting of C$_{1-6}$ alkyl, C$_{1-6}$ alkoxy, halogen, NR$^a$R$^b$, nitro and cyano;
R$^a$ and R$^b$ (i) taken independently in each occurrence are hydrogen or C$_{1-6}$ alkyl or (ii) taken together are (CH$_2$)$_n$ wherein n is 4-6.

7. A compound according to claim 6 wherein:
R$^1$ is chloro;
R$^3$ is C$_{1-6}$ alkyl or phenyl C$_{1-3}$ alkyl wherein said phenyl is optionally substituted with 1 to 3 groups independently selected in each occurrence from the group consisting of C$_{1-6}$ alkyl, C$_{1-6}$ alkoxy, halogen, NR$^a$R$^b$, nitro and cyano;
R$^4$ is C$_{1-6}$ alkyl;
R$^a$ and R$^b$ (i) taken independently in each occurrence are hydrogen or C$_{1-6}$ alkyl or (ii) taken together are (CH$_2$)$_n$ wherein n is 4-6.

8. A compound according to claim 1 wherein said compound is of formula Ia and R$^1$ is C$_{1-6}$ alkyl.

9. A compound according to claim 8 wherein R$^2$ is C$_{1-6}$ alkyl and R$^3$ is C$_{1-6}$ alkyl or phenyl-C$_{1-3}$ alkyl wherein said phenyl is optionally substituted with 1 to 3 groups independently selected in each occurrence from the group consisting of C$_{1-6}$ alkyl, halogen or C$_{1-6}$ alkoxy.

10. A compound according to claim 1 wherein said compound is of formula Ia and R$^1$ is COR$^5$ and R$^5$ is NR$^c$R$^d$.

11. A compound according to claim 10 wherein:
R$^2$ is C$_{1-6}$ alkyl, C$_{3-7}$ cycloalkyl or NR$^a$R$^b$;
R$^3$ is C$_{1-6}$ alkyl or phenyl-C$_{1-3}$ alkyl wherein said phenyl is optionally substituted with 1 to 3 groups independently selected in each occurrence from the group consisting of C$_{1-6}$ alkyl, C$_{1-6}$ alkoxy, halogen, NR$^a$R$^b$, nitro and cyano;
R$^4$ is C$_{1-6}$ alkyl;
R$^c$ and R$^d$ are hydrogen.

12. A compound according to claim 11 where R$^2$ is methyl, R$^3$ is 4-F-benzyl, R$^4$ is tert-Bu.

13. A compound of claim 1 which compound is selected from the group consisting of:

N-{3-[(S)-5-tert-butyl-1-(4-fluoro-benzyl)-4-hydroxy-2-oxo-2,5-dihydro-1H-pyrrol-3-yl]-2-methyl-1,1-dioxo-1,4-dihydro-1λ$^6$-benzo[1,4]thiazin-7-yl}-methanesulfonamide;

N-{3-[(S)-5-tert-butyl-4-hydroxy-1-(3-methyl-butyl)-2-oxo-2,5-dihydro-1H-pyrrol-3-yl]-2-chloro-1,1-dioxo-1,4-dihydro-1λ$^6$-benzo[1,4]thiazin-7-yl}-methanesulfonamide;

N-{3-[(S)-5-tert-butyl-1-(4-fluoro-benzyl)-4-hydroxy-2-oxo-2,5-dihydro-1H-pyrrol-3-yl]2-chloro-1,1-dioxo-1,4-dihydro-1λ$^6$-benzo[1,4]thiazin-7-yl}-methanesulfonamide;

ethanesulfonic acid {3-[(S)-5-tert-butyl-1-(4-fluoro-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-amide;

cyclopropanesulfonic acid {3-[(S)-5-tert-butyl-1-(4-fluoro-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-amide;

N-{3-[(S)-5-tert-butyl-1-(4-fluoro-3-methyl-benzyl)-4-hydroxy-2-oxo-2,5-dihydro-1H-pyrrol-3-yl]2-chloro-1,1-dioxo-1,4-dihydro-1λ$^6$-benzo[1,4]thiazin-7-yl}-methanesulfonamide;

ethanesulfonic acid {3-[(S)-5-tert-butyl-1-(4-fluoro-3-methyl-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-amide;

cyclopropanesulfonic acid {3-[(S)-5-tert-butyl-1-(4-fluoro-3-methyl-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-amide;

N-{3-[(S)-5-tert-butyl-1-(3-chloro-4-fluoro-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-methanesulfonamide;

ethanesulfonic acid {3-[(S)-5-tert-butyl-1-1-(3-chloro-4-fluoro-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-amide;

cyclopropanesulfonic acid {3-[(S)-5-tert-butyl-1-(3-chloro-4-fluoro-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-amide;

ethanesulfonic acid {3-[(S)-5-tert-butyl-4-hydroxy-1-(3-methyl-butyl)-2-oxo-2,5-dihydro-1H-pyrrol-3-yl]-2-chloro-1,1-dioxo-1,4-dihydro-1λ$^6$-benzo[1,4]thiazin-7-yl}-amide;

N-{3-[(S)-5-tert-butyl-1-(5-fluoro-pyridin-2-ylmethyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-methanesulfonamide;

N-[3-((S)-1-Benzyl-5-tert-butyl-4-hydroxy-2-oxo-2,5-dihydro-1H-pyrrol-3-yl)-2-chloro-1,1-dioxo-1,4-dihydro-1λ$^6$-benzo[1,4]thiazin-7-yl]-methanesulfonamide;

N-{3-[(S)-5-tert-butyl-1-(2-cyclopentyl-ethyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-methanesulfonamide;

N-{3-[(S)-5-tert-butyl-1-(4-fluoro-3-methoxy-benzyl)-4-hydroxy-2-oxo-2,5-dihydro-1H-pyrrol-3-yl]-2-chloro-1,1-dioxo-1,4-dihydro-1λ$^6$-benzo[1,4]thiazin-7-yl}-methanesulfonamide;

N-{3-[(S)-5-tert-butyl-1-(2-cyclopropyl-ethyl)-4-hydroxy-2-oxo-2,5-dihydro-1H-pyrrol-3-yl]-2-chloro-1,1-dioxo-1,4-dihydro-1$\lambda^6$-benzo[1,4]thiazin-7-yl}-methanesulfonamide;

N-{3-[(S)-5-tert-butyl-1-(4-fluoro-3-methyl-benzyl)-4-hydroxy-2-oxo-2,5-dihydro-1H-pyrrol-3-yl]-2-fluoro-1,1-dioxo-1,4-dihydro-1$\lambda^6$-benzo[1,4]thiazin-7-yl}-methanesulfonamide;

N-{3-[(S)-5-tert-butyl-1-(4-fluoro-benzyl)-4-hydroxy-2-oxo-2,5-dihydro-1H-pyrrol-3-yl]-2-cyano-1,1-dioxo-1,4-dihydro-1$\lambda^6$-benzo[1,4]thiazin-7-yl}-methanesulfonamide;

3-[(S)-5-tert-butyl-1-(4-fluoro-benzyl)-4-hydroxy-2-oxo-2,5-dihydro-1H-pyrrol-3-yl]-7-methanesulfonylamino-1,1-dioxo-1,4-dihydro-1$\lambda^6$-benzo[1,4]thiazine-2-carboxylic acid dimethylamide;

3-[(S)-5-tert-butyl-1-(4-fluoro-benzyl)-4-hydroxy-2-oxo-2,5-dihydro-1H-pyrrol-3-yl]-7-methanesulfonylamino-1,1-dioxo-1,4-dihydro-1$\lambda^6$-benzo[1,4]thiazine-2-carboxylic acid amide;

cyclopropanesulfonic acid {3-[(S)-5-tert-butyl-4-hydroxy-1-(3-methyl-butyl)-2-oxo-2,5-dihydro-1H-pyrrol-3-yl]-2-chloro-1,1-dioxo-1,4-dihydro-1$\lambda^6$-benzo[1,4]thiazin-7-yl}-amide;

N-{3-[(S)-5-tert-butyl-1-(3-chloro-4-fluoro-benzyl)-4-hydroxy-2-oxo-2,5-dihydro-1H-pyrrol-3-yl]-2-cyano-1,1-dioxo-1,4-dihydro-1$\lambda^6$-benzo[1,4]thiazin-7-yl}-methanesulfonamide;

N-{3-[(S)-5-tert-butyl-1-(4-fluoro-3-methoxy-benzyl)-4-hydroxy-2-oxo-2,5-dihydro-1H-pyrrol-3-yl]-2-cyano-1,1-dioxo-1,4-dihydro-1$\lambda^6$--benzo[1,4]thiazin-7-yl}-methanesulfonamide;

N-{3-[(S)-5-tert-butyl-1-(4-fluoro-3-methyl-benzyl)-4-hydroxy-2-oxo-2,5-dihydro-1H-pyrrol-3-yl]-2-cyano-1,1-dioxo-1,4-dihydro-1$\lambda^6$-benzo[1,4]thiazin-7-yl}-methanesulfonamide;

N-{3-[(S)-5-tert-butyl-4-hydroxy-1-(3-methyl-butyl)-2-oxo-2,5-dihydro-1H-pyrrol-3-yl]-2-cyano-1,1-dioxo-1,4-dihydro-1$\lambda^6$-benzo[1,4]thiazin-7-yl}-methanesulfonamide;

N-{3-[(S)-5-tert-butyl-1-(2-cyclopropyl-ethyl)-4-hydroxy-2-oxo-2,5-dihydro-1H-pyrrol-3-yl]-2-cyano-1,1-dioxo-1,4-dihydro-1$\lambda^6$-benzo[1,4]thiazin-7-yl}-methanesulfonamide;

N-{3-[(S)-5-tert-butyl-1-(2-cyclopentyl-ethyl)-4-hydroxy-2-oxo-2,5-dihydro-1H-pyrrol-3-yl]-2-cyano-1,1-dioxo-1,4-dihydro-1$\lambda^6$-benzo[1,4]thiazin-7-yl}-methanesulfonamide;

3-[(S)-5-tert-butyl-4-hydroxy-1-(3-methyl-butyl)2-oxo-2,5-dihydro-1H-pyrrol-3-yl]-7-methanesulfonylamino-1,1-dioxo-1,4-dihydro-1$\lambda^6$-benzo[1,4]thiazine-2-carboxylic acid amide;

3-[(S)-5-tert-butyl-1-(4-fluoro-3-methyl-benzyl)-4-hydroxy-2-oxo-2,5-dihydro-1Hpyrrol-3-yl]-7-methanesulfonylamino-1,1-dioxo-1,4-dihydro-1$\lambda^6$-benzo[1,4]thiazine-2-carboxylic acid amide;

N-{3-[(S)-5-tert-butyl-4-hydroxy-1-(3-methyl-butyl)-2-oxo-2,5-dihydro-1H-pyrrol-3-yl]-2-methyl-1,1-dioxo-1,4-dihydro-1$\lambda^6$-benzo[1,4]thiazin-7-yl}-methanesulfonamide; or, a pharmaceutically acceptable salt thereof.

14. A method for treating a disease caused by the Hepatitis C Virus (HCV) infection comprising administering to a patient in need thereof, a therapeutically effective quantity of a compound according to claim 1.

15. A pharmaceutical composition comprising a therapeutically effective quantity of a compound according to claim 1 admixed with at least one pharmaceutically acceptable carrier, diluent or excipient.

* * * * *